(12) United States Patent
Hu et al.

(10) Patent No.: US 8,048,450 B2
(45) Date of Patent: Nov. 1, 2011

(54) AQUEOUS DISPERSION OF HYDROGEL NANOPARTICLES WITH INVERSE THERMOREVERSIBLE GELATION

(75) Inventors: Zhibing Hu, Denton, TX (US); Xiaohu Xia, Evanston, IL (US)

(73) Assignee: University of North Texas, Denton, TX (US)

( * ) Notice: Subject to any disclaimer, the term of this patent is extended or adjusted under 35 U.S.C. 154(b) by 0 days.

(21) Appl. No.: 10/581,678

(22) PCT Filed: Dec. 9, 2004

(86) PCT No.: PCT/US2004/041331
§ 371 (c)(1),
(2), (4) Date: Sep. 20, 2006

(87) PCT Pub. No.: WO2005/055982
PCT Pub. Date: Jun. 23, 2005

(65) Prior Publication Data
US 2007/0116765 A1 May 24, 2007

Related U.S. Application Data

(60) Provisional application No. 60/528,081, filed on Dec. 9, 2003.

(51) Int. Cl.
*A61K 9/14* (2006.01)
(52) U.S. Cl. ........ 424/486; 424/487; 977/702; 977/897; 977/906
(58) Field of Classification Search .................. None
See application file for complete search history.

(56) References Cited

U.S. PATENT DOCUMENTS

| | | | |
|---|---|---|---|
| 5,135,627 A * | 8/1992 | Soane | 204/455 |
| 5,403,893 A | 4/1995 | Tanaka et al. | |
| 6,632,457 B1 | 10/2003 | Sawhney | |
| 6,639,014 B2 | 10/2003 | Pathak et al. | |
| 6,749,868 B1 | 6/2004 | Desai et al. | |

OTHER PUBLICATIONS

Kubota et al., Journal of Applied Polymer Science, 1998, vol. 70, p. 1027-1034.*
Kubota et al., Journal of Applied Polymer Science, 2001, vol. 80, p. 798-805.*
Gan & Lyon, J. Am. Chem. Soc., 2001, vol. 123, No. 31, p. 7511-7517.*
Plucktaveesak et L., XIIIth International Congress on Rheology, Cambridge, UK, 2000, 3-307-309.*
Hennink & Nostrum, Advanced Drug Delivery, 2002, vol. 13, p. 13-36.*
Kubota et al., Journal of Applied Polymer Science, 2001, vol. 80, p. 789-805.*
Dhara et al. Macromol Chem. Phys. 2001, vol. 202, p. 3617-3623.*
Gan & Lyon, J. Am. Chem. Soc., 2001, vol. 123, No. 31, p. 7511-7517.*
Hennink & Nostrum, Advanced Drug Delivery, 2002, vol. 13, p. 13-36.*
Bouillot et al., Colloid Polym Sci, 2000, vol. 278, p. 74-79.*
Qiu et al., Advanced Drug Delivery, 2001, vol. 53, p. 321-339.*
Cai et al., Journal of Applied Polymer Science, 2002, vol. 83, p. 169-178.*
Jeong et al., Advanced Drug Delivery Reviews, 2002, vol. 54, p. 37-51.*
Kurisawa et al., Journal of Controlled Release, 1998, vol. 54, p. 191-200.*
Jones et al., Macromolecules, 2000, vol. 33, p. 8301-8306.*
Hennink & Nostrum, Advanced Drug Delivery Reviews, 2002, vol. 54, p. 13-36.*
Gan et al., J Am. Chem. Soc., 2001, vol. 123, p. 7511-7517.*
Benee, L. S., Snowden, M. J., Chowdhry, B. Z., Langmuir, 2002, 18, 6025.

(Continued)

*Primary Examiner* — Kade Ariani
(74) *Attorney, Agent, or Firm* — Jackson Walker L.L.P.

(57) ABSTRACT

An aqueous dispersion of hydrogel nanoparticles and methods of making the aqueous dispersion of hydrogel nanoparticles having an interpenetrating polymer network ("IPN") are described. The uniformed sized mono-disperse IPN nanoparticles have inverse thermo gelation properties that allow therapeutic medications to be uniformly distributed in a liquid form of the aqueous dispersion of hydrogel nanoparticles. Such medications can then be released from a solid form of the aqueous dispersion of hydrogel nanoparticles in time dependant manor.

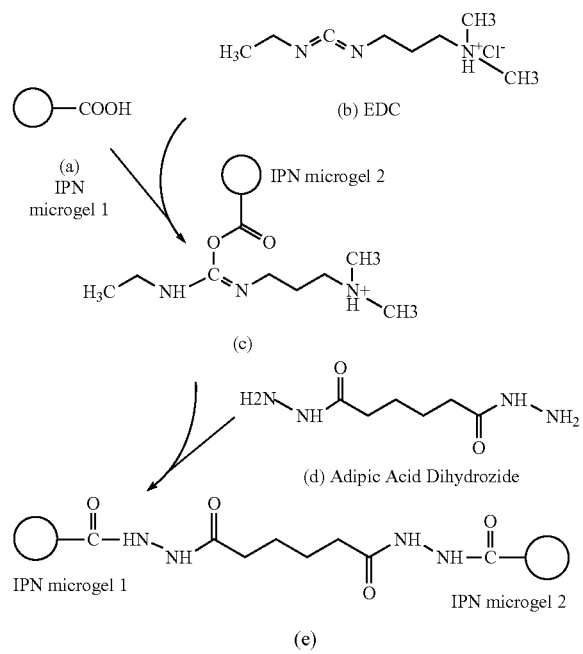

44 Claims, 29 Drawing Sheets

OTHER PUBLICATIONS

Bouillot, P., Vincent, B. Colloid and Polymer Science 2000, 278, 74-79.
Bromberg, L.E., Ron, E.S., Temperature-responsive gels and thermogelling polymer matrices for protein and peptide delivery, Adv. Drug Deliv. Rev. 31 (1998) 197.
Chen, L., Gong, J., Osada, Y. Macromolecular Rapid Communications 2002, 23(3), 171-174.
Durand, D., Hourdet, Synthesis and thermoassociative properties in aqueous solution of graft copolymers containing poly(N-isopropylacrylamide) side chains, Polymer 40 (1999) 4941.
Gao, J., Frisken, B. J., Langmuir, 2003, 19, 5217-5222.
Gao, J., Hu, Z., Langmuir, 2002, 18 (4), 1360-1367.
Gutowska, Y.H., Bae, H., Jacobs, J., Feijen, Sung Wan Kim, Macromolecules, 1994, 27, 4167.
Han, C.K., Bae, Y. H., Polymer 1998, 39, 2809-2814.
Hayakawa, M. Onda, T. Tanaka, T., and K. Tsujii, K., Langmuir 1997, 13, 3595.
Hirotsu, S., Hirokawa, Y., Tanaka, T. J. Chem. Phys. 1987, 87, 1392.
Hu, X., Xia, H., Hydrogel nanoparticle dispersions with inverse thermoreversible gelation, Adv. Mat. 16 (2004) 305.
Ilmain, T. Tanaka, E. Kokufuta, Volume transition in a gel driven by hydrogen bonding, Nature (London, United Kingdom) 349 (1991) 400.
Jeong, B., Kim, S. W., Bae, Y. H.,Adv. Drug Del. Rev. 2002, 54, 37-51.
Jones, C. D., Lyon, L.A., Macromolecules 2000, 33, 8301-8306.
Katono, H., Maruyama, A., Sanui, K., Ogata, N., Okano, T., Sakurai, Y. J Control Rel 1991, 16, 215-227 273:464-472.
Lee, K., and Asher, S. A., J. Am. Chem. Soc., 122, 9534-9537 (2000).
Pelton, R., Adv. Colloid Interface Sci. 2000, 85, 1-33.
Routh, A. F., Vincent, B., Langmuir, 2002, 18, 5366-5369.
Sassi, A. P. Shaw, A. J. Han, S. M., Blanch, H. W. and Prausnitz, J. M., Partitioning of proteins and small biomolecules in temperature- and pH-sensitive hydrogels, Polymer 37 (1996) 2151.
Tsujii, K., Hayakawa, M., Onda, T., Tanaka, T., Macromolecules 1997, 30, 7397.
Wang, C. J., Hu, Z. B., Chen, Y. Y., Li, Y. Macromolecules 1999, 32, 1822-1827.
Weissman, J.M., Sunkara, H. B., Tse, A. S., Asher, S. A., Science 1996, 274, 959-960.
Wu, J.Z., Zhou, B., Hu, Z. B., Phys. Rev. Lett. 2003, 90, 048304.
Wu, J.Z., Zhou, C.S. Macromolecules 1996, 29, 1574.
Wu, J.Z., Huang, G., Hu, Z. B., Macromolecules 2003, 36, 440-448.
Xia, X.H., Z. B. Hu, Synthesis and light scattering study of nanoparticles with interpenetrating polymer networks, Langmuir 20 (2004) 2094.
Yoshida, R., Uchida, K., Kaneko, Y., Sakai, K., Kikuchi, A., Sakurai, Y., and Okano, T., Comb-type grafted hydrogels with rapid de-swelling response to temperature changes, Nature 374 (1995) 240.
Holtz, S. A. Asher, Nature 1997, 389, 829-832. c) L. Liu, P. Li, and S. A. Asher, Nature, 397, 141-144 (1998).

* cited by examiner

Table 1. Comparison of PNIPA and IPN Nanoparticles

| | $R_h$(nm) | $R_g$(nm) | $R_g/R_h$(a.u.) | $A_2$(mol*cm³/g²) | Mw (g/mol) | Density(g/cm³) | PNIPA:PAA ratio |
|---|---|---|---|---|---|---|---|
| PNIPA | 121 | 98 | 0.81 | $8.9 \times 10^{-5}$ | $8.137 \times 10^7$ | $1.82 \times 10^{-2}$ | 1 : Nothing |
| IPN | 202 | 143 | 0.71 | $9.5 \times 10^{-5}$ | $2.341 \times 10^8$ | $1.13 \times 10^{-2}$ | 1 : 1.88 |

Figure 26

Table 2. Synthesis conditions for IPN Nanoparticles

| | $R_h$ / nm | Precursor PNIPAm $R_h$ / nm | Reaction temp. / °C | Reaction time /mins | Precursor PNIPAm PD.I.* | IPN PD.I | PNIPAm:PAA |
|---|---|---|---|---|---|---|---|
| IPN110 | 110 | 90 | 23 | 23 | 1.05 | 1.08 | 1 : 0.13 |
| IPN155 | 155 | 125 | 23 | 23 | 1.03 | 1.07 | 1 : 0.50 |

* PD.I stands for Polydispersity Index.

Figure 27

Table 3. Time required for 60% of the loading drugs being released at 37°C

| From 5.25% microgel networks | M.W. 40K | M.W. 70K | M.W. 500K | M. W. 2M |
|---|---|---|---|---|
| IPN155 (minutes) | Less than 30 | 300 | 300 | 1300 |
| IPN110 (minutes) | Less than 30 | 320 | 1000 | 4000 |
| IPN155/IPN110 (1:1) (minutes) | — | — | 1000 | 4600 |

Figure 28

Table 4 a detailed comparison between Cluster 3 and IPN microgels.

| | $R_h$(nm) | $R_g$(nm) | $R_g/R_h$(a.u.) | P.D.I. | Mw (g/mol) | Density(g/cm³) | LCST |
|---|---|---|---|---|---|---|---|
| IPN155 | 155 | 110 | 0.71 | 1.03 | $2.80 \times 10^8$ | $1.43 \times 10^{-2}$ | 33°C |
| Nanocluster3 | 235 | 178 | 0.75 | 1.04 | $9.30 \times 10^9$ | $1.36 \times 10^{-2}$ | 33°C |

Figure 29

AQUEOUS DISPERSION OF HYDROGEL NANOPARTICLES WITH INVERSE THERMOREVERSIBLE GELATION

RELATED APPLICATIONS

This application claims priority to a U.S. Provisional Patent Application filed Dec. 9, 2003, Ser. No. 60/528,081, entitled "Hydrogel Nanoparticle Dispersions with Inverse Thermoreversible Gelation," with Hu et al., listed as inventors, the entire content of which is hereby incorporated by reference.

BACKGROUND

The present invention pertains to aqueous dispersions of hydrogel nanoparticles and methods of making mono-disperse interpenetrating polymer network ("IPN") nanoparticles. More specifically, the IPN nanoparticles are made from a first polymer that is formed by polymerizing a first mixture of monomers, a cross linking agent, and an initiator to form a first polymer nanoparticle. The first polymer nanoparticle is swollen with a second combination of monomers and cross linking agents, which is subsequently polymerized to form the mono-disperse IPN nanoparticles having unique thermally induced gelling properties. This thermally induced viscosity change, and in situ hydrogel formation allows for therapeutic medications to be mixed into a liquid form of the nanoparticles and be uniformly distributed in a solid hydrogel at an elevated temperature without being destroyed by harsh chemical processes typically used to solidify a liquid. Additionally, the solid hydrogel allows the controlled time release of medications. This invention also includes compositions and methods for the synthesis of the soft nanoclusters composed of several crosslinked IPN nanoparticles building blocks.

Generally, effective drug therapies usually require that: (a) a certain concentration level of a medication (called the therapeutic index) be maintained for; (b) a certain period of time. For example, a systemically administered medication may quickly elevate the concentration level of the medication, but many delivery systems have the potential to be inefficient and are accompanied with toxic side effects resulting from high doses. In contrast, systemic administration of controlled release formulations can accomplish both objectives with a more efficient delivery of the drug that may reduce side effects. Additionally, implantation of a drug delivery system may further improve the efficiency for utilizing a locally specific drug.

Generally, hydrogels are materials that absorb solvents (such as water), undergo rapid swelling without discernible dissolution, and maintain three-dimensional networks capable of reversible deformation. Hydrogels may be uncrosslinked or crosslinked. Uncrosslinked hydrogels are typically able to absorb water but do not dissolve due to the presence of hydrophobic and hydrophilic regions. Covalently crosslinked networks of hydrophilic polymers, including water soluble polymers, are traditionally denoted as hydrogels in the hydrated state. A number of aqueous hydrogels have been used in various biomedical applications, such as, soft contact lenses, and wound management. Additionally, hydrogels have been previously utilized as drug delivery systems, for example: U.S. Pat. No. 6,639,014 issued to Pathak, et al., on Oct. 28, 2003, titled "Multiblock Biodegradable Hydrogels for Drug Delivery and Tissue Treatment, ("the '014 Patent"); and U.S. Pat. No. 6,632,457 issued to Sawhney on Oct. 14, 2003, titled "Composite Hydrogel Drug Delivery Systems," ("the '457 Patent").

Hydrogels containing two IPN's are the subject of intensive investigation (Ilmain, F., Tanaka, T., Kokufuta, E. Nature (London, United Kingdom) 1991, 349, 400-1). This is because an IPN hydrogel usually exhibits properties that a hydrogel with the random co-polymerization of two monomers does not have. For example, the IPN of poly(acrylic acid) ("PAAc") and polyacrylamide ("PAAM") undergoes the volume phase transition driven by cooperative "zipping" interactions between the molecules which result from hydrogen bonding (Ilmain, F., Tanaka, T., Kokufuta, E. Nature (London, United Kingdom) 1991, 349, 400-1). In addition to the improved mechanical properties which usually come from the reinforcement between two interpenetrating networks, (Sperling, L. H. Adv. Chem. Ser. 1994, 239, 12). an IPN hydrogel can have a preferred direction for swelling by pre-stressing one of them (poly-N-isopropylacrylamide ("PNIPAM")) before the gelation of the other one (polyacrylamide ("PAAM")) takes place (Wang, C. J., Hu, Z. B., Chen, Y. Y., Li, Y. Macromolecules 1999, 32, 1822-1827). A well-designed hydrogel with an IPN structure shows an upper critical solution temperature without a volume change (Chen, L., Gong, J., Osada, Y. Macromolecular Rapid Communications 2002, 23(3), 171-174). Two polymer chain networks in an IPN gel can be sensitive independently to two different external stimuli. Such hydrogels have been employed for controlled drug delivery (Katono, H., Sanui, K., Ogata, N., Okano, T., Sakurai, Y. *Polym J* 1991, 23, 1179-1189; Katono, H., Maruyama, A., Sanui, K., Ogata, N., Okano, T., Sakurai, Y. *J Control Rel* 1991, 16, 215-227 273:464-472; Gutowska, Y. H., Bae, H., Jacobs, J., Feijen, Sung Wan Kim, *Macromolecules*, 1994, 27, 4167; Park, T. G., Choi, H. K. *Macromol. Rapid Commun.* 1998, 19, 167-172) The PNIPAM gel undergoes the volume phase transition at $T_c=34°$ C. and has been used often as one of the components in an IPN gel (Hirotsu, S., Hirokawa, Y., Tanaka, T. J. Chem. Phys. 1987, 87, 1392; Wu, C., Zhou, S. Macromolecules 1996, 29, 1574; Benee, L. S., Snowden, M. J., Chowdhry, B. Z., Langmuir, 2002, 18, 6025; Routh, A. F., Vincent, B., Langmuir, 2002, 18, 5366-5369; Woodward, N. C., Chowdhry, B. Z., Snowden, M. J., Leharne, S. A., Griffiths, P. C., Winnington, A. L., Langmuir, 2003, 19, 3202-3211; Gao, J.; Frisken, B. J., Langmuir, 2003, 19, 5217-5222). Its phase transition temperature remains the same if the PNIPAM is incorporated in an IPN matrix. However, the random copolymerization results in shifting $T_c$ depending on the hydrophilic/hydrophobicity of the co-monomer.

IPN microgel particles have been synthesized because they are more effective as delivery systems than macroscopic gels for agrochemical or medical applications (Bouillot, P., Vincent, B. *Colloid and Polymer Science* 2000, 278, 74-79). A comparison of the swelling behavior of the random P(AAc-co-Aam) particles and PAAc/PAAm IPN microgels has been made using temperature and pH as the triggers (Bouillot, P., Vincent, B. *Colloid and Polymer Science* 2000, 278, 74-79). Jones and Lyon, on the other hand, showed multiresponsive core-shell microgels that consist of a weakly interpenetrating polymer network core and a shell (Jones, C. D., Lyon, L. A. *Macromolecules* 2000, 33, 8301-8306). These microgels were prepared by precipitation polymerization at 70° C. in aqueous media. In the synthesis of the shell polymer, the collapsed particles serve as nuclei for further polymerization, thereby resulting in preferential growth of the existing particles over the nucleation of new ones (Jones, C. D., Lyon, L. A. *Macromolecules* 2000, 33, 8301-8306). The IPN nanoparticles of this invention are substantially free from the typical collapsed core and shell polymers described above.

A method to synthesize an IPN microgel of PNIPAM/PAAc is described herein. The Jones and Lyon's method (as described in (Jones, C. D., Lyon, L. A. *Macromolecules* 2000, 33, 8301-8306) was extended by lowering the reaction temperature below the lower critical solution temperature of the PNIPAM polymer and by controlling reaction time so that the reaction was stopped once the interpenetrating polymer network was formed at room temperature. The synthesis and light scattering characterization of these microgels, which displays the same $T_c$ as the PNIPAM but shrinks less than the PNIPAM above $T_c$ are shown. The semi-dilute aqueous solutions of the PNIPAM-PAAc IPN microgels exhibit unusually inverse thermo-reversible gelation. In contrast to polymer solutions of poly(NIPAM-co-AAc) that have the inverse thermoreversible gelation, the disclosed system can self-assemble into an ordered structure, displaying bright colors (T. Kato, M. Yokoyama, A. Takahashi, *Colloid & Polym. Sci.* 1978, 256, 15; M. Almgren, P. Bahadur, M. Jansson, P. Li, W. Brown, A. J. Bahadur, *Colloid & Interface Sci.* 1992, 151, 157; P. Alexandridis, T. A. Hatton, *Colloidal Surfaces A: Physicochem. Eng. Aspects* 1995, 96, 1-46; C. K. Han, Y. H. Bae, *Polymer* 1998, 39, 2809-2814; B. Jeong, S. W. Kim, Y. H. Bae, *Adv. Drug Del. Rev.* 2002, 54, 37-51).

The IPN nanoparticles aqueous dispersions possessing the sharp inverse thermo-gelation property tunable in a very narrow temperature range (1-2° C.) are useful in a number of biomedical applications that may include tissue engineering scaffold, bio-adhesive, cell culture matrix and controlled drug delivery. More specifically, the focus of this invention pertains to the advantages in the controlled drug loading and release aspects. Thermally responsive bulk gels are usually formed through free radical polymerization of monomers (R. Yoshida, K. Uchida, Y. Kaneko, K. Sakai, A. Kikuchi, Y. Sakurai, and T. Okano, Comb-type grafted hydrogels with rapid de-swelling response to temperature changes, Nature 374 (1995) 240; Y. H. Bae, T. Okano, and S. W. Kim, Thermosensitive polymers as on-off switches for drug release, Makromolecular Chemistry Rapid Communication 8 (1987) 481; T. Okano, Y. H. Bae, H. Jacobs, and S. W. Kim, Thermally on-off switching polymers for drug permeation and release, Journal of Controlled Release 11 (1990) 255; Y. H. Bae, T. Okano, and S. W. Kim, "On-off" thermocontrol of solute transport. I. Temperature dependence of swelling of N-isopropylacrylamide networks modified with hydrophobic components in water, Pharmaceutical Research 8 (1991) 531; Y. H. Bae, T. Okano, and S. W. Kim, "On-off" thermocontrol of solute transport. II. Solute release from thermosensitive hydrogels, Pharmaceutical Research 8 (1991) 624). Bulk gels have a permanent structure of covalently bonded polymer chains. In contrast, the IPN nanoparticle networks discussed here have a thermally reversible structure, and the physical bonds between the neighboring particles can be turned on of off by switching the temperature above or below the gelation temperature. Furthermore, a drug molecule is usually loaded in a bulk gel by either mixing drug with monomer, initiator and crosslinked, or allowing a bulk gel to swell to equilibrium in a suitable drug solution (Y. H. Bae, T. Okano, S. W. Kim, Hydrogels, Swelling and Drug Loading and Release, Pharma. Res. 9 (1992) 283). The first approach may suffer from the possibility of side reaction that can damage the drug, while the second approach may exclude large molecules, like proteins, from the gel network (L. E. Bromberg, E. S. Ron, Temperature-responsive gels and thermogelling polymer matrices for protein and peptide delivery, Adv. Drug Deliv. Rev. 31 (1998) 197). In contrast, a drug molecule can be mixed into the nanoparticle dispersion at room temperature. At body temperature (37° C.), the particles were bonded by physical bonds to form a gel to allow the drug slowly diffusing out of the nanoparticle network. Because there is no chemical reaction involved, the drug molecule could be entrapped nanoparticle network safely.

Additionally, the IPN microgels could be used as a special building block to build the mono-dispersed soft nanoclusters due to the strong inter-particles hydrophobic attraction even in a relatively dilute environment at T>34° C. In this disclosure, the mono-disperse soft nanoclusters were synthesized by zero-distance covalent bonding a certain number of microgels composed of poly-acrylic acid ("PAAc") and poly(N-isopropylacrylamide) ("PNIPAM") interpenetrating networks ("IPN"). The kinetics of the nanoclusters formation was obtained by measuring the particles hydrodynamic radius ("$R_h$") change as a function of the reaction time. Individual nanocluster was characterized by both dynamic and static light scattering, and compared to its building block IPN microgels. The number of IPN microgels in each nanocluster can be statistically manipulated through controlling the reaction duration. The nanoclusters undergo a reversible volume phase transition in response to the temperature changes, but have no obvious sensitivity to pH. In contrast to its building block IPN microgels, the nanoclusters exhibited an enhanced de-swell ability upon temperature increase. This novel soft nanomaterial possesses unique pomegranate-like architecture and may have great potential for injection drug loading and delivery applications.

A preferred embodiment of the present invention pertains to a composition and process for synthesizing mono-disperse nanoparticles having the interpenetrating structure of poly(N-isopropylacrylamide) and poly(acrylic acid). The preferred IPN nanoparticles microgels have physically crosslinked IPN's and a property of reversible gel formation. The physical structures of specific crosslinked mono-disperse nanoparticle IPN microgels allow these materials to be utilized as timed drug release carriers. One of ordinary skill in the art can utilize the principles described herein to design and fabricate other hydrogel nano/micro-particles water dispersions possessing having similar inverse thermoreversible gelation properties. The preferred nanoparticles include but are not limited to: poly(acrylic acid)/poly(N-isopropylacrylamide) IPN nanoparticles; poly(acrylic acid)/hydroxypropylcellulose IPN nanoparticles; dextran/poly(N-isopropylacrylamide) IPN nanoparticles and dextran/hydroxylpropylcellulose IPN nanoparticles.

SUMMARY

A first aspect of the current invention pertains to aqueous dispersions of hydrogel nanoparticles that have a uniformed size. These nanoparticles have a first polymer interpenetrating a second polymer forming an interpenetrating polymer network ("IPN"). In a preferred embodiment, the first polymer comprises poly(N-isopropylacrylamide) ("PNIPAM") and the second polymer comprises poly(acrylic acid) ("PAAc"). The preferred PNIPAM/PAAc IPN nanoparticles have a weight ratio of about 1:1.88, and the total polymer concentration is in a range from about 1.25 wt % to about 5.25 wt % in distilled water. The IPN nanoparticles of this invention are substantially free of a shell and core polymer configuration. Additionally, the aqueous dispersion of IPN nanoparticles can undergo a reversible phase transition in response to a stimulus, such as a temperature change, pH change, solvent concentration change or a combination of changes. For example, stimulating the aqueous dispersion of IPN nanoparticles by increasing the temperature above a gelation temperature ("Tg") induces a volume phase transition and a reversible inverse thermo-thickening property, which results the transformation of the IPN nanoparticles from a low-viscous fluid to a gel when heated above the Tg. The PNIPAM/PAAc IPN nanoparticles have a Tg of about 34° C. A pH change that is below the pKa of the second polymer induces a volume phase transition. A preferred hydrogel also contains a biologically active material that may be a drug, a pro-drug, a protein, or a nucleic acid. The mono-disperse nanoparticles have a uniformed sized hydrodynamic radius that is in the range from about 75 nm to about 200 nm.

A second aspect of the current invention pertains to a method of preparing an interpenetrating polymer network ("IPN") of mono-disperse nanoparticles. The method includes the steps of: (a) providing a first mono-dispersed polymer nanoparticle; (b) adding to the first mono-dispersed polymer nanoparticle a second monomer, a second cross linking agent, a second initiator and an activator forming a nanoparticle solution; (c) mixing the nanoparticle solution for a period of time at a second temperature to form the IPN of mono-disperse nanoparticles; and (d) isolating the IPN of mono-dispersed nanoparticles. The first mono-dispersed polymer nanoparticle was prepared by mixing a first monomer, a first cross linking agent, and a first initiator under a substantially oxygen gas free environment at a first temperature. In a preferred embodiment the substantially oxygen gas free environment included sparging the first polymer components with nitrogen gas to remove dissolved oxygen gas prior to polymerization. Similarly, the first monomer, the first cross linking agent, the second monomer, the second cross linking agent are substantially free of dissolved oxygen gas. The first and second polymer components were sparged with nitrogen gas to remove dissolved oxygen gas. The method further comprises: (e) mixing the isolated IPN of mono-dispersed nanoparticles with a biologically active material (e.g. a drug, a pro-drug, a protein, or a nucleic acid) at a third temperature. In a preferred embodiment, the first mono-dispersed polymer nanoparticle comprises poly(N-isopropylacrylamide); the second monomer comprises acrylic acid; the first cross linking agent comprises N,N'-methylenebisacrylamide; the first initiator comprises potassium persulfate; the second initiator comprises ammonium persulfate; and the activator comprises TEMED; the period of time is less than 130 minutes; first temperature is about 70° C. and second temperature is about 21° C. The IPN nanoparticles produced using the method of this invention are substantially free of a shell and core polymer configuration and have a uniformed sized hydrodynamic radius that is in the range from about 75 nm to about 200 nm.

A third aspect of the current invention is a nanocluster of cross-linked interpenetrating polymer network ("IPN") nanoparticles. The preferred nanocluster comprises a first IPN nanoparticle cross-linked to a second IPN nanoparticle via a cross linking group. The first IPN nanoparticle and second IPN nanoparticle each comprise a first polymer interpenetrating a second polymer, the nanoparticles are substantially free from a shell and core polymer configuration, as discussed above. The cross linking group comprises adipic acid dihydrazide. In a preferred embodiment, the nanocluster comprises at least a third IPN nanoparticle that is cross-linked to the first and second IPN nanoparticles. Additionally, the nanocluster can undergo a reversible phase transition in response to a stimulus, such as a temperature change, pH change, solvent concentration change or a combination of changes. For example, stimulating a solution of nanoclusters by increasing the temperature above a gelation temperature ("Tg") induces a volume phase transition and a reversible inverse thermo-thickening property, which results the transformation of the nanoclusters from a low-viscous fluid to a gel when heated above the Tg. The average hydrodynamic radius of the nanocluster is in the range from about 155 nm to about 250 nm. The nanocluster may further comprise a biologically active material, such as a drug, a pro-drug, a protein, or a nucleic acid.

A fourth aspect of the current invention includes a method of preparing a nanocluster of cross-linked interpenetrating polymer network ("IPN") nanoparticles. The method comprises: providing a dispersion of IPN nanoparticles; adding a first cross linking agent and a second cross linking agent to the IPN mono-dispersed nanoparticles, forming an IPN cross linking solution; and heating the cross linking solution to a first temperature for a period of time. The preferred IPN mono-dispersed nanoparticles were discussed above and have a uniformed size and comprise a first polymer interpenetrating a second polymer and is substantially free from a shell and core polymer configuration. The first cross linking agent comprises 1-ethyl-3(3-dimethylaminopropyl)carbodiimide hydrochloride ("EDAC"), and the second cross linking agent comprises adipic acid dihydrazide. The nanocluster of cross-linked IPN's an average hydrodynamic radius in the range from about 155 nm to about 250 nm; the period of time is less than 130 minutes; and the first temperature is about 44° C. The method may further comprise mixing the nanocluster of cross-linked IPN's with a biologically active material at a second temperature, which may include a drug, a pro-drug, a protein, or a nucleic acid. The second temperature is below a gelation temperature ("Tg") of the nanocluster of cross-linked IPN's, which is about 33° C. in a preferred embodiment.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 26 shows Table 1, a comparison of PNIPAM and IPN nanoparticles.

FIG. 27 shows Table 2, the synthesis conditions for IPN nanoparticles.

FIG. 28 shows Table 3, the time required for 60% of the loading drugs being released at 37° C.

FIG. 29 shows Table 4, a detailed comparison between Cluster3 and IPN microgels.

DETAILED DESCRIPTION OF PREFERRED EMBODIMENTS

Figure 1:
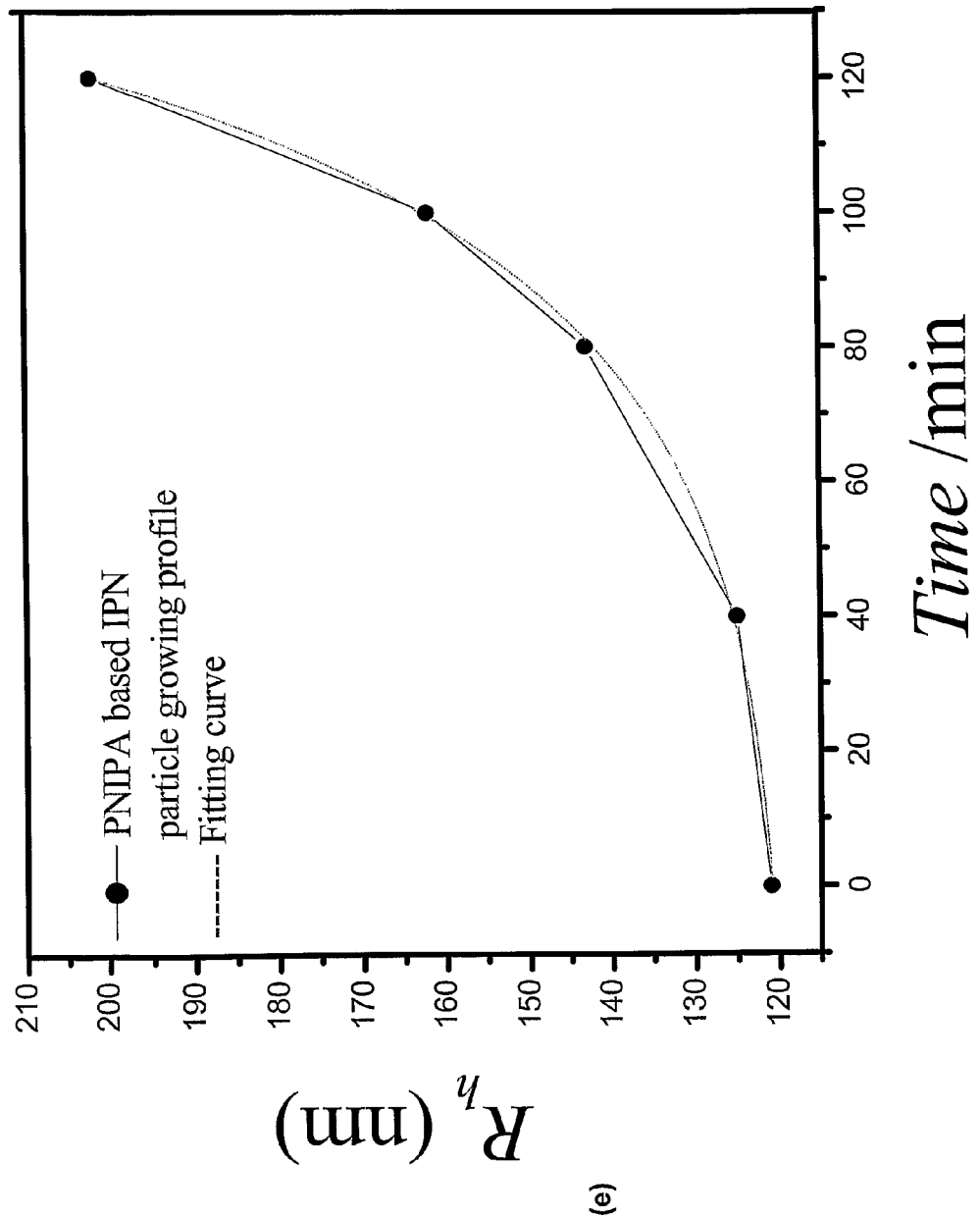
FIG. 1 shows the time dependent hydrodynamic radius ("$R_h$") of the particles during IPN microgel formation. Here 10 ml of aliquot solution was taken from the reaction container at the different reaction times for dynamic light scattering analysis. All samples have the same polymer concentration of $5.0 \times 10^{-6}$ g/ml based on PNIPAM solid content. The pH values were adjusted between 6.5 and 7.0.

The present invention pertains to hydrogels and methods of making hydrogels having an interpenetrating polymer network ("IPN"). More specifically, a first polymer is formed by polymerizing a first mixture of monomers, a cross linking agent, and an initiator to form a first polymer network nanoparticle. The first polymer network nanoparticle is swollen with the second combination of monomers and cross linking agents and polymerized to form mono-disperse IPN nanoparticles with unique inverse temperature gelling properties. In a preferred embodiment, the uniformed sized mono-disperse IPN nanoparticles also contain a therapeutic drug that can be used to release the drug "in vivo" in time dependant manor.

The present invention comprises hydrogels, nanoclusters, methods for making hydrogels, and methods for making nanoclusters. The compositions, processes, techniques, and apparatus use for synthesizing hydrogels, nanoparticles and nanoclusters with an interpenetrating structure of poly(N-isopropylacrylamide) and poly(acrylic acid) are provided to further illustrate this invention and the manner in which it may be carried out. Examples are provide that demonstrate the reaction kinetics of the IPN microgel formation including: a laser light scattering study of IPN and PNIPA nanoparticles; a temperature induced volume phase transition and the thermo-thickening property; and a pH induced volume phase transition. Additionally, a rich phase diagram is provided to illustrate the properties and phase behavior of colloidal systems exemplified by the semi-dilute IPN nanoparticle solutions. More specifically, the aqueous dispersion of the small IPN nanoparticles having a hydrodynamic radius less than 100 nm is capable of forming a transparent nanoparticle network by gently heating the nanoparticles from room temperature (~21° C.) to body temperature (~37° C.). This thermally induced viscosity change, and in situ hydrogel formation allows for drugs to be mixed into a liquid form of the nanoparticles and be uniformly distributed in a solid hydrogel at body temperature without being destroyed by chemical processes to solidify the liquid. Additionally, the solid hydrogel allows the controlled release of drugs. This invention also includes compositions and methods for the synthesis of the soft nanoclusters composed of the IPN nanoparticles building blocks. The principles to design and the processes to fabricate other hydrogel nano/micro-particles dispersions possessing the similar inverse thermoreversible gelation behavior, which include but not limited to poly(acrylic acid)/poly(N-isopropylacrylamide) core-shell nanoparticles, poly(acrylic acid)/hydroxypropylcellulose core-shell nanoparticles, dextran/poly(N-isopropylacrylamide) core-shell microparticles and dextran/hydroxylpropylcellulose core-shell microparticles.

EXAMPLES

The following examples are provided to further illustrate this invention and the manner in which it may be carried out. It will be understood, however, that the specific details given in the examples have been chosen for purposes of illustration only and not be construed as limiting the invention.

Example 1

The process, technique and apparatus for synthesizing of mono-disperse IPN nanoparticles with the interpenetrating structure of poly(N-isopropylacrylamide) and poly(acrylic acid) are described herein.

1.1 Materials: N-isopropylacrylamide was purchased from Polysciences, Inc. Dodecyl sulfate, sodium salt 98%; potassium persulfate; acrylic acid 99%; and N,N'-Methylenebisacrylamide 99% were purchased from Aldrich. Tetra-methyl-ethylene-diamine (TEMED) and ammonium persulfate were bought from Bio-Rad Laboratories. Water for sample preparation was distilled and deionized to a resistance of 18.2 MΩ by a MILLIPORE system, and filtered through a 0.22 µm filter to remove particulate matter.

1.2. PNIPAM microgel preparation: The polymerization [20] of NIPAM was carried out in a flask equipped with a magnetic stirrer and a nitrogen feed: 3.8 g N-isopropylacrylamide, 0.066 g N,N'-Methylenebisacrylamide and 0.15 g sodium dodecyl sulfate ("SDS") were dissolved in 240 g distilled water under continuous stirring for one hour. The solution was being nitrogen purged for 40 min before setting into a 70° C. hot bath. 0.166 g potassium persulfate, which was dissolved in 20 ml water, was then added to initiate the emulsion polymerization. The reaction last for 4 hours under nitrogen atmosphere. The reaction temperature was kept at (70±0.5)° C. The final PNIPAM microgel size was controlled by adding different surfactant concentration: the larger the concentration, the smaller particle size. The PNIPAM microgels were prepared with two different sizes (hydrodynamic radius Rh are 121 nm and 170 nm, respectively) for the next step IPN synthesis.

All PNIPAM particles were purified via dialysis (Spectra/Por 7 dialysis membrane, MWCO 10'000, VWR) against frequent changes of stirring water for 2 weeks at room temperature. The final PNIPAM microgel concentrations were adjusted to $1.35 \times 10^{-2}$ g/ml.

1.3. IPN microgel synthesis: The preparation of IPN microgels was based on the above PNIPAM microgels: 35 g PNIPAM microgel solution was diluted ten times with distilled water. 0.5 g N,N'-Methylenebisacrylamide and 2.3 g acrylic acid were then added. The solution was bubbled for 1 hour with nitrogen gas. The initiators (0.2 g ammonium persulfate) and accelerator (0.2 g TEMED) were separately dissolved in water and added rapidly to the solution, making the final solution volume into 370 ml. The reaction last for 120 min under nitrogen atmosphere, and temperature was well regulated at (21±1)° C. with a water bath. To gather reaction kinetic information, 10 ml aliquot solution was taken from reaction container at different time since reaction started. All aliquots were dialyzed for future dynamic light scattering analysis. The resultant microgels have the structure of PNIPAM-PAAc interpenetrating polymer network (IPN), rather than the PNIPAM-PAAc core-shell structure.

1.4. Turbidity measurement: Absorbance measurements (wavelengths from 200 to 1100 nm) were made on an Agilent 8453 UV-Vis Spectrometer with a 1-cm optical path length quartz cell.

1.5 Reaction kinetics of the IPN microgel formation: The kinetics of the IPN particle formation was studied by measuring the hydrodynamic radius ($R_h$) of the particles as a function of reaction time as shown in FIG. 1. Here 10 ml of aliquot solution was taken from the reaction container at different reaction times, then purified via dialysis and finally diluted to $5 \times 10^{-6}$ g/ml with distilled water for dynamic light scattering analysis. The solution concentration is based on the PNIPAM solid content. As one can see from FIG. 1, initially, the PNIPAM microgels as seeds have an average hydrodynamic radius of 121 nm at 21° C. The value of $R_h$ increases little during the first one hour, but dramatically in the following 60 minutes. Further reaction for 10 more minutes leads to precipitation. The data are well described by an equation of $R_h = 119.1 + 1.77 e^{t/\tau}$, where the characterization time $\tau = 31$ min. The particles grow faster as the reaction temperature increases.

Figure 2:
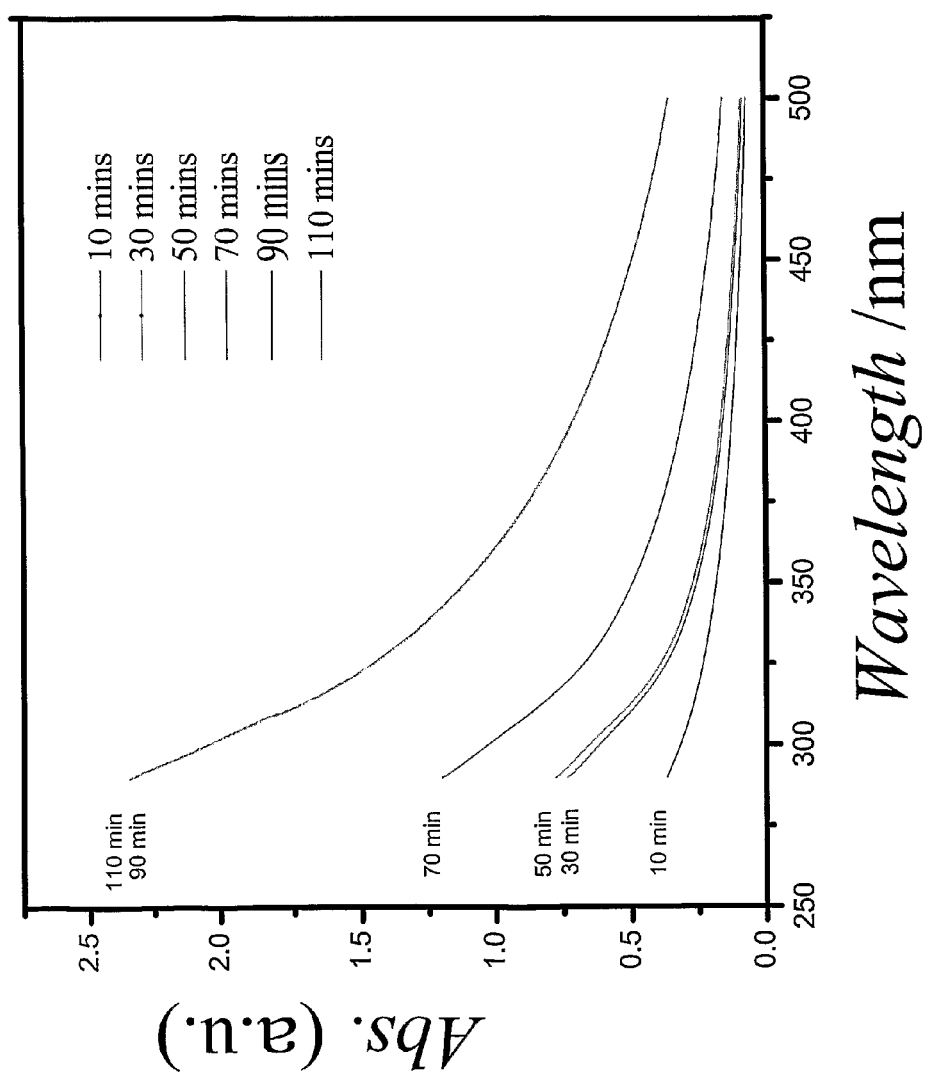
FIG. 2 shows the turbidity change of the reacting solution during IPN microgel formation, as measured by UV/Vis spectrometer. Here 10 ml of aliquot solution was taken from the reaction container at the different reaction times and the PNIPAM concentration for each sample is $1.27 \times 10^{-3}$ g/ml. The absorption wavelength is ranged from 290 nm to 500 nm.

Visual observation revealed that the solution turned from translucent to blurred blue to white and finally to precipitation during the IPN growth. This observation was quantified by measuring time dependent turbidity using an UV/Vis spectrometer as shown in FIG. 2. Since the continuous reaction for 130 minutes lead to precipitation, the reaction was stopped at 120 min.

Figure 25:
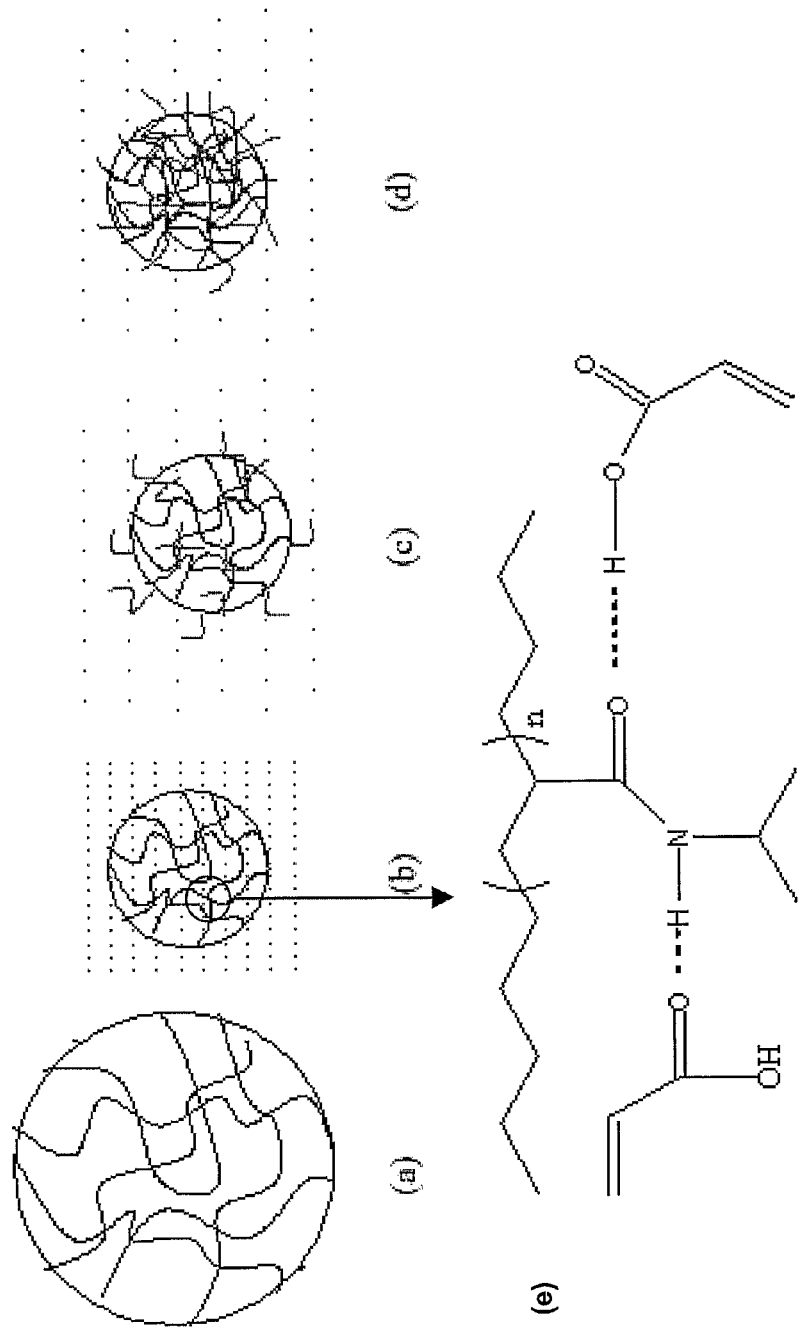
FIG. 25 shows an IPN microgel synthesis: (a) a pure PNIPAM microgel as a seed; (b) shrunk PNIPAM microgel under the effect of electrolyte acrylic acid, the red dots stand for the acrylic acid monomers; (c) polymerization of the acrylic acid; (d) the resultant IPN microgels of PNIPAM-PAAc; (e) shows an enlarged chemical diagram of (b) having the hydrogen bonding between PNIPAM and acrylic acid represented by the dotted line as indicated.

The IPN formation may be understood in terms of the polymerization of acrylic acid within each PNIPAM microgel. Although the PNIPAM microgels shrink slightly in acrylic acid solution due to an electrolyte effect, they swell enough at 21° C. (below LCST) allowing the acrylic acid monomer to diffuse into their interior. The interaction between the —COOH group on acrylic acid and the —CONH— group on PNIPAM, in the form of monomeric or dimeric hydrogen bonding, [1] causes the preferred growth of the PAAc network around the PNIPAM network. As the hydrophilic PAAc concentration gradually increases in the PNIPAM skeleton, the IPN particle swells more by absorbing more water. Later reaction mainly happened on the IPN particle surface where there is much more un-reacted acrylic acid monomers available, resulting in fast growth of the particle size. The particles therefore underwent the structure change from PNIPAM to IPN and finally to IPN-PAAc core-shell throughout the reaction. The mechanism for the IPN synthesis is schematically shown in FIG. 25. To demonstrate the importance of hydrogen bonding for the IPN formation and growth, sodium acrylate was used to replace acrylic acid as an interpenetrating agent. Indeed, without hydrogen bonding PNIPAM-sodium acrylate cannot form an IPN structure as shown that there is no change in either turbidity or particle size within 4 hours, monitored by UV/Vis spectrometry and dynamic light scattering.

Figure 3:
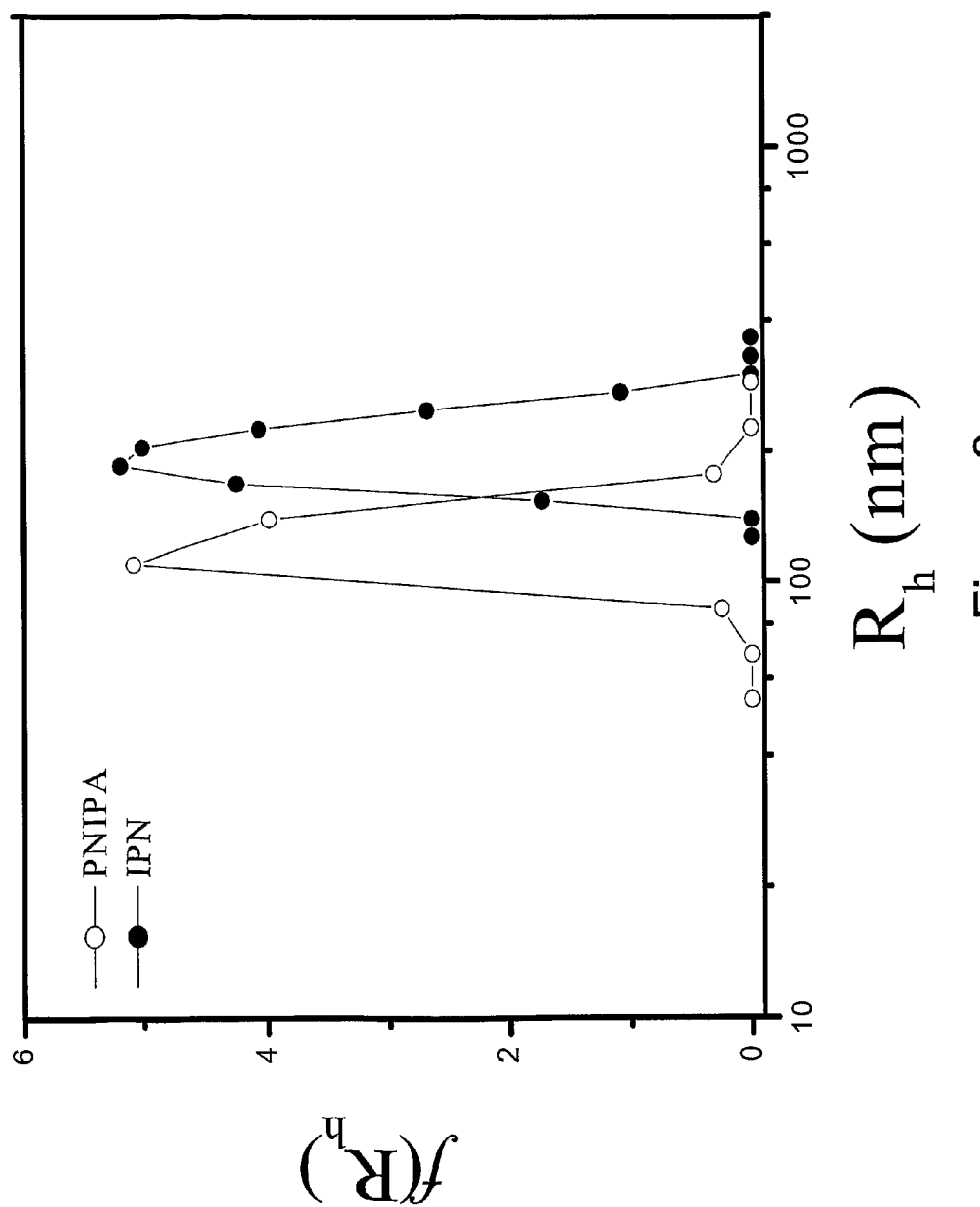
FIG. 3 shows the particle size distribution of the IPN microgel and its precursor PNIPAM microgel at 21° C., as measured by dynamic light scattering. The scattering angle is at 90°.

1.6. Comparison of PNIPAM and IPN microgels at 21° C.: PNIPAM and IPN microgels were characterized and compared using dynamic and static light scattering. Both PNIPAM and IPN nanoparticles were diluted to $5.0 \times 10^{-6}$ g/ml with distilled water with pH values around 6.5-7.0. The particles size and distribution are shown in FIG. 3, in which the PNIPAM microgels are narrowly distributed with $R_h$ around 121 nm, while IPN around 202 nm. The calculated polydispersity index (PD.I) for PNIPAM and IPN are 1.068 and 1.07, respectively. Here PD.I is defined as $$1 + \frac{\mu_2}{<\Gamma>^2}$$

with $$\mu_2 = \int_0^\infty G(D)(D - <D>)^2 \, dD$$

and $$D = \frac{K_b T}{6\pi\eta <R_h>}.$$

Increased particle size and their narrow distribution demonstrate that PAAc interpenetrates into the PNIPAM particles and the formation of new homo-PAAc particles during IPN synthesis is negligible.

Figure 4:
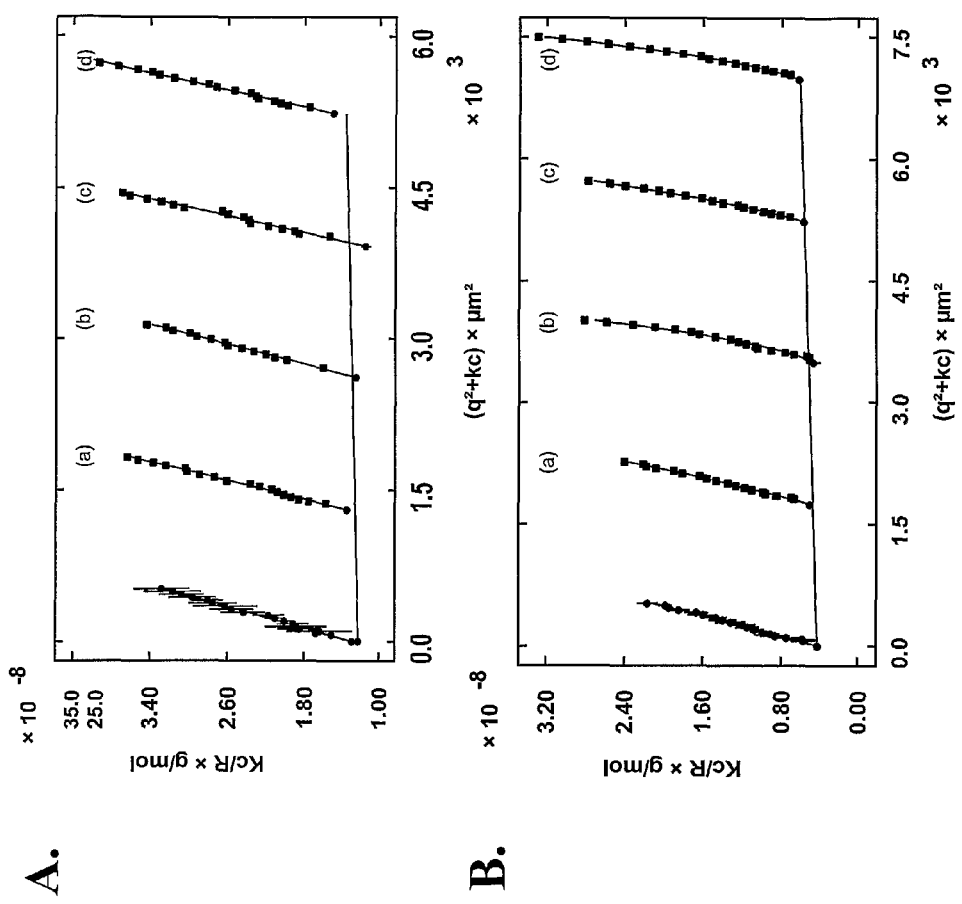
FIG. 4 shows the Zimm plots of static light scattering for (a) PNIPAM microgel and (b) IPN microgel at 21° C. The polymer concentration varies from $2.5 \times 10^{-6}$ g/ml to $1.0 \times 10^{-5}$ g/ml for both.

FIG. 4(a) shows the Zimm plot for the pure PNIPAM aqueous solution at 25° C., with sample concentration varying from $2.5 \times 10^{-6}$ g/ml to $1.0 \times 10^{-5}$ g/ml. The value of dn/dc used here is 0.166 cm$^3$/g, measured by a refractometer. From the extrapolation of $KC/R_{vv}(q)$ in Eq. 1 to the zero angle and zero concentration, the molar mass $M_w$, the second virial coefficient $A_2$, and the radius of gyration $<R_g>$ are determined to be $8.14 \times 10^7$ g/mol, $8.90 \times 10^{-5}$ mol*cm$^3$/g$^2$, and 98 nm, respectively. By combining DLS and SLS results, the ratio of $<R_g>/<R_h>$ was found to be 0.80, which is close to the theoretical value of $(3/5)^{1/2}$ for a uniform hard sphere. The density of a pure PNIPAM nanoparticle ($\rho$) in water is estimated about $1.82 \times 10^{-2}$ g/cm$^3$ at 25° C. in water using the equation $4/3 * \pi R_h^3 \rho = M_w/N_A$, where $R_h$ and $M_w$ are obtained from DLS and SLS, respectively, and $N_A$ is Avogadro's number.

From the Zimm plot of static light scattering for IPN microgels in water as shown in FIG. 4(b), the molar mass $M_w$, the radius of gyration $<R_g>$ and second virial coefficient $A_2$ are $2.34 \times 10^8$ g/mol, 144 nm and $9.50 \times 10^{-5}$ cm$^3$/g$^2$, respectively. The value of dn/dc used here is 0.102 cm$^3$/g. The increased value of $A_2$ for the IPN indicates that the IPN is more hydrophilic than its PNIPAM precursor at a neutral pH environment. As a result, the IPN contains more water than the PNIPAM does. Combining DLS and SLS results, the obtained ratio of $<R_g>/<R_h>$ was 0.71. It suggests that the polymers are uniformly distributed. The average density of this IPN ($\rho$) is estimated about $1.13 \times 10^{-2}$ g/cm$^3$ at 25° C. in water. The detailed comparison between PNIPAM and IPN microgels is listed in FIG. 26 (Table 1).

The weight ratio of PAAc to PNIPAM in each IPN microgel is determined to be 1.88:1 by calculating the molar weight ratio of the IPN ($M_w$ $2.34 \times 10^8$ g/mol) to the PNIPAM ($8.14 \times 10^7$ g/mol). The value is very close to 1.82:1, measured by the evaporation method. If the reaction lasted longer, the weight ratio increased correspondingly.

Figure 5:
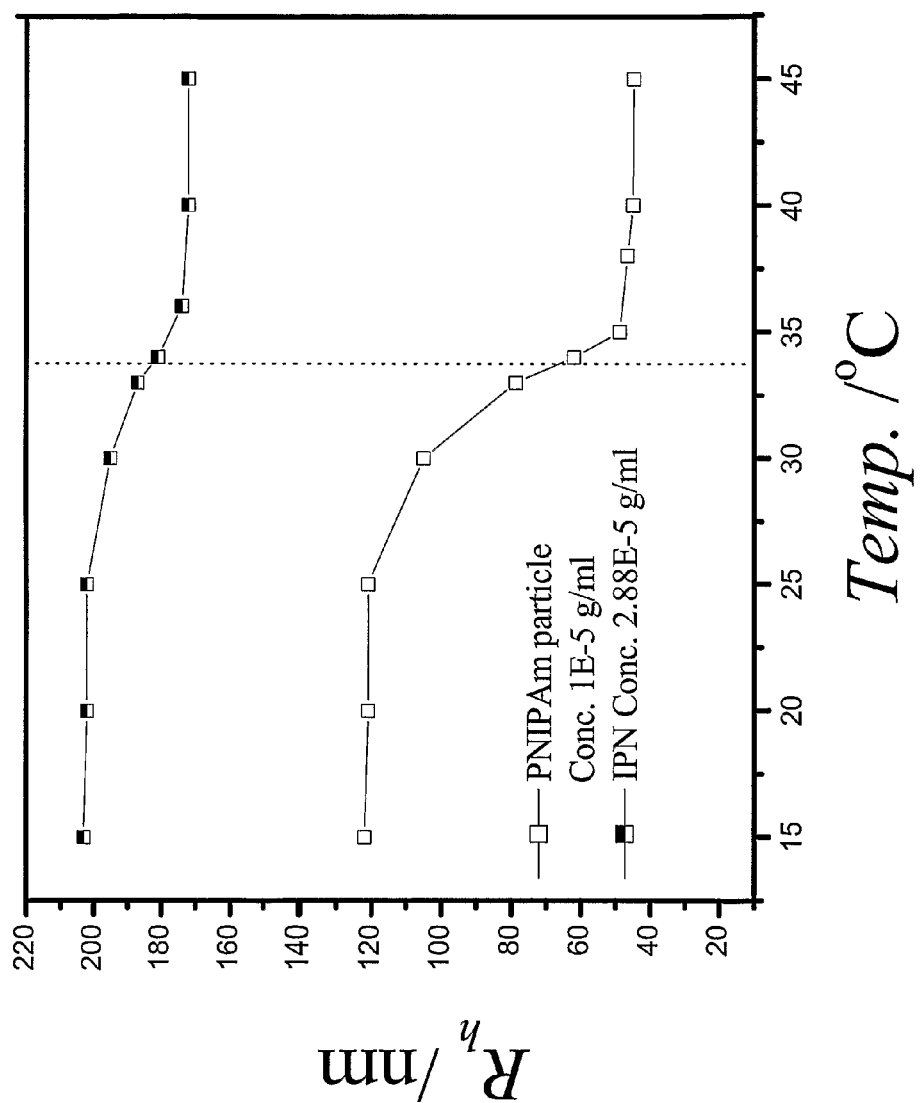
FIG. 5 shows the temperature induced volume phase transition for PNIPAM and IPN microgels. They both exhibit the same volume phase transition temperature.

1.7. Temperature induced volume phase transition and the thermo-thickening property: The IPN microgel undergoes the volume phase transition at 34° C. that is the same as the one for the PNIPAM microgel as shown in FIG. 5. For a randomly co-polymerized PAAc/PNIPAM gel, the volume phase transition temperature increases with PAAc concentration.[8] The volume change of the IPN below and above the volume transition temperature is smaller than that of the PNIPAM. This is because the PAAc network in the IPN is not sensitive to the temperature change and can reduce the shrinkage of the PNIPAM network.

Figure 6:
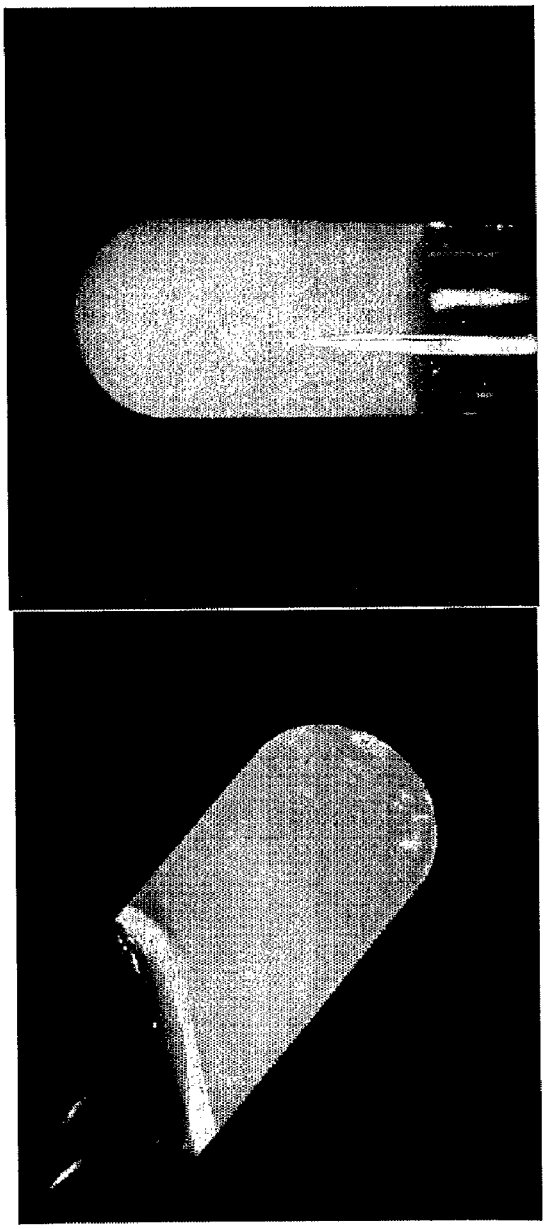
FIG. 6 shows a black and white illustration of the viscosity change of the IPN semi-dilute aqueous solution with polymer concentration of $2.5 \times 10^{-2}$ g/ml. Below ~34° C., the dispersion is a fluid and above ~34° C., the dispersion becomes a solid.

For diluted IPN and PNIPAM solution ($5.0 \times 10^{-6}$ g/ml), the interaction between particles can be neglected. However, as polymer concentration increases, the interaction between particles plays an important role that causes viscosity to change as the temperature changes. Specifically, a semi-diluted IPN aqueous solution with polymer concentration 2.5% g/ml is found to exhibit an inverse thermoreversible gelation at pH above 5. That is, when the system is heated to above the gelation temperature $T_g = 34°$ C., it undergoes a transformation from a low-viscous fluid to a gel. This behavior is completely reversible. FIG. 6 shows the comparison of IPN semi-diluted solution at room temperature (left) and 40° C. (right). The PNIPAM in the IPN matrix provides physical cross linking bonds between particles via a temperature-dependent interparticle potential, [25] while PAAc in the IPN in the neutral pH provides ionic charges that are temperature-independent and prevent the collapse of the particles into an aggregate. In contrast to polymer solutions that have the inverse thermoreversible gelation such as methyl cellulose, [16] poly(ethylene oxide)-poly(propylene oxide)-poly(ethylene oxide) triblock copolymers,[17] PNIPAM-PAAc copolymers,[18] and degradable triblock copolymers,[19] the particles of this system can self-assemble into an ordered structures, displaying colors due to the Bragg diffraction.[26]

Figure 7:
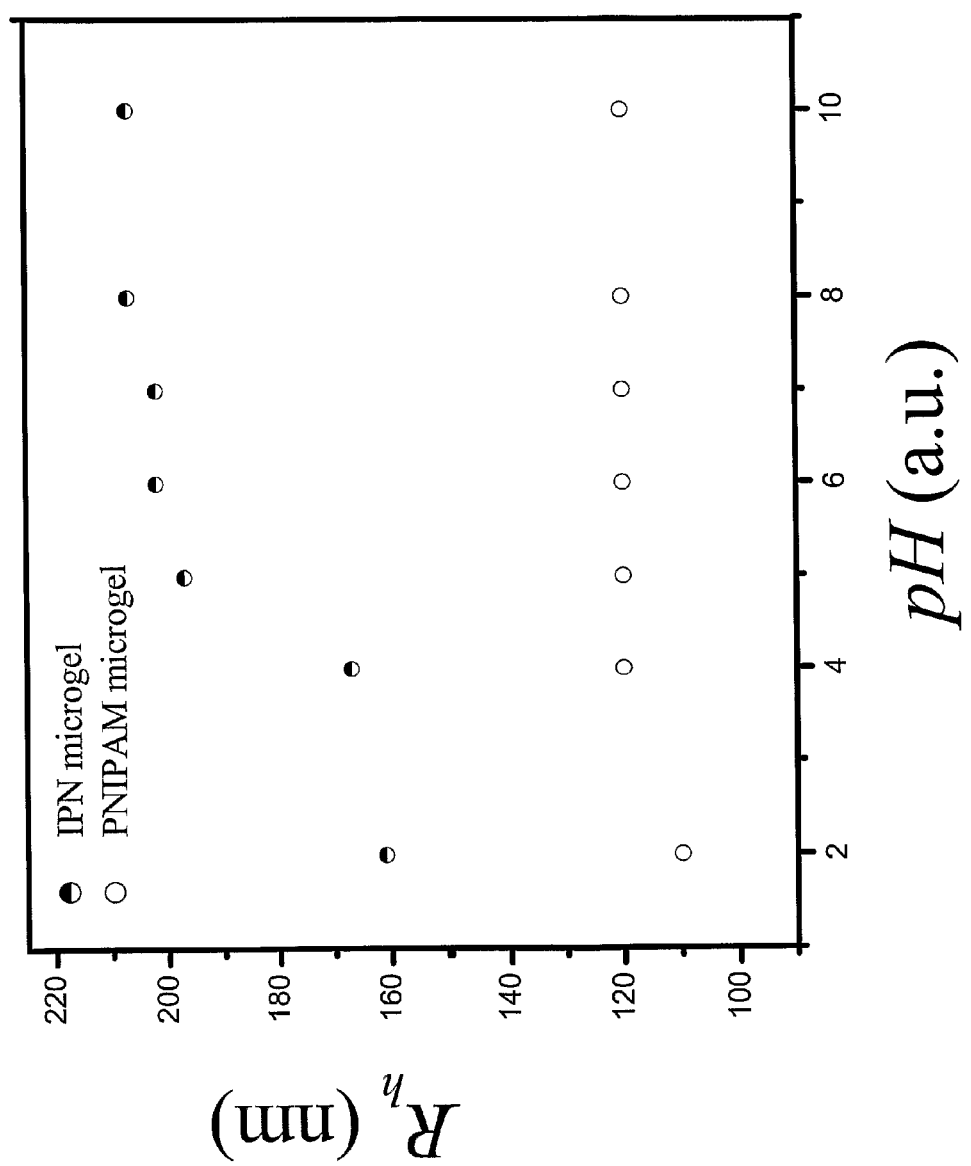
FIG. 7 shows the pH induced volume phase transition for PNIPAM and IPN microgels.
Figure 8:
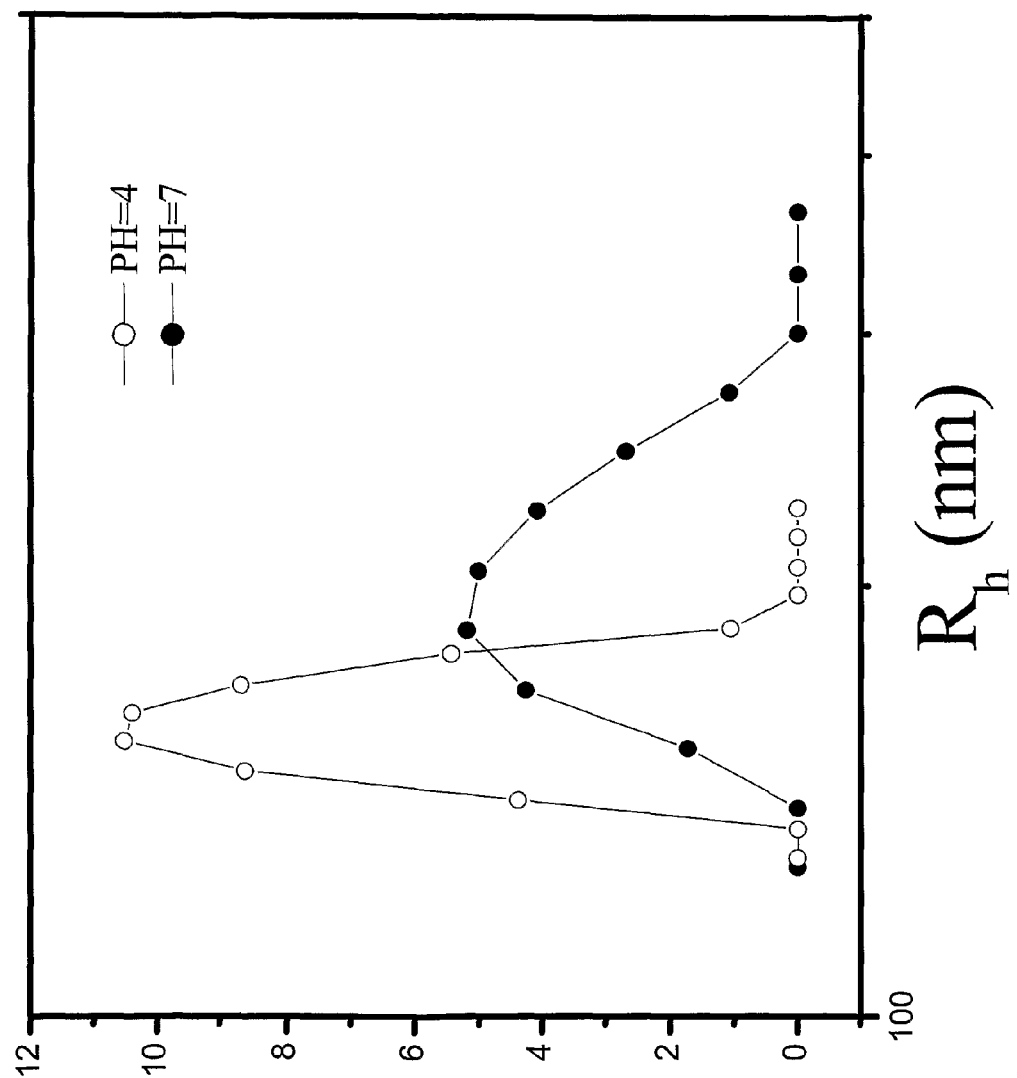
FIG. 8 shows the particle size distributions of IPN microgels at different pH environments.

1.8. pH induced volume phase transition The IPN microgel possesses a pH sensitivity due to the contribution of the PAAc. The values of $R_h$ for IPN and PNIPAM microgels with the polymer concentration of $5.0 \times 10^{-6}$ g/ml at 21° C. are shown in FIG. 7 as a function of pH. The pH values were adjusted by adding either hydrochloric acid or sodium hydroxide to the solution. As shown in FIG. 7, there is a sharp drop of $R_h$ for the IPN microgel from 200 nm to 165 nm as the pH decreases from 5 to 4. In the pH range of 5-10, the $R_h$ is around 200 nm without aggregation as demonstrated by a constant scattering light intensity. PAAc is in an ionic state when the pH is above its pKa 4.7 and is hydrophilic. However, at pH<4.7, the PAAc is the molecular state and becomes hydrophobic, repelling water out from its network. This causes the shrinkage of the IPN at low pH value. It's interesting to note that the extent of pH induced the IPN shrinkage is about the same as that of the temperature induced the IPN shrinkage, both from 200 nm to around 160 nm. As expected, there is no particle size variation observed for the PNIPAM microgel in the pH range of 4-10. The slight decrease occurred at pH=2 may be due to the electrolyte effect. The comparison of the IPN microgel size distributions at pH 4 and 7 is shown in FIG. 8. The PD.I for IPN microgel at pH 4 and 7 are 1.02 and 1.07, respectively. It indicates that the IPN has a narrower size distribution after the shrinkage at pH 4.

Example 2

Figure 9:
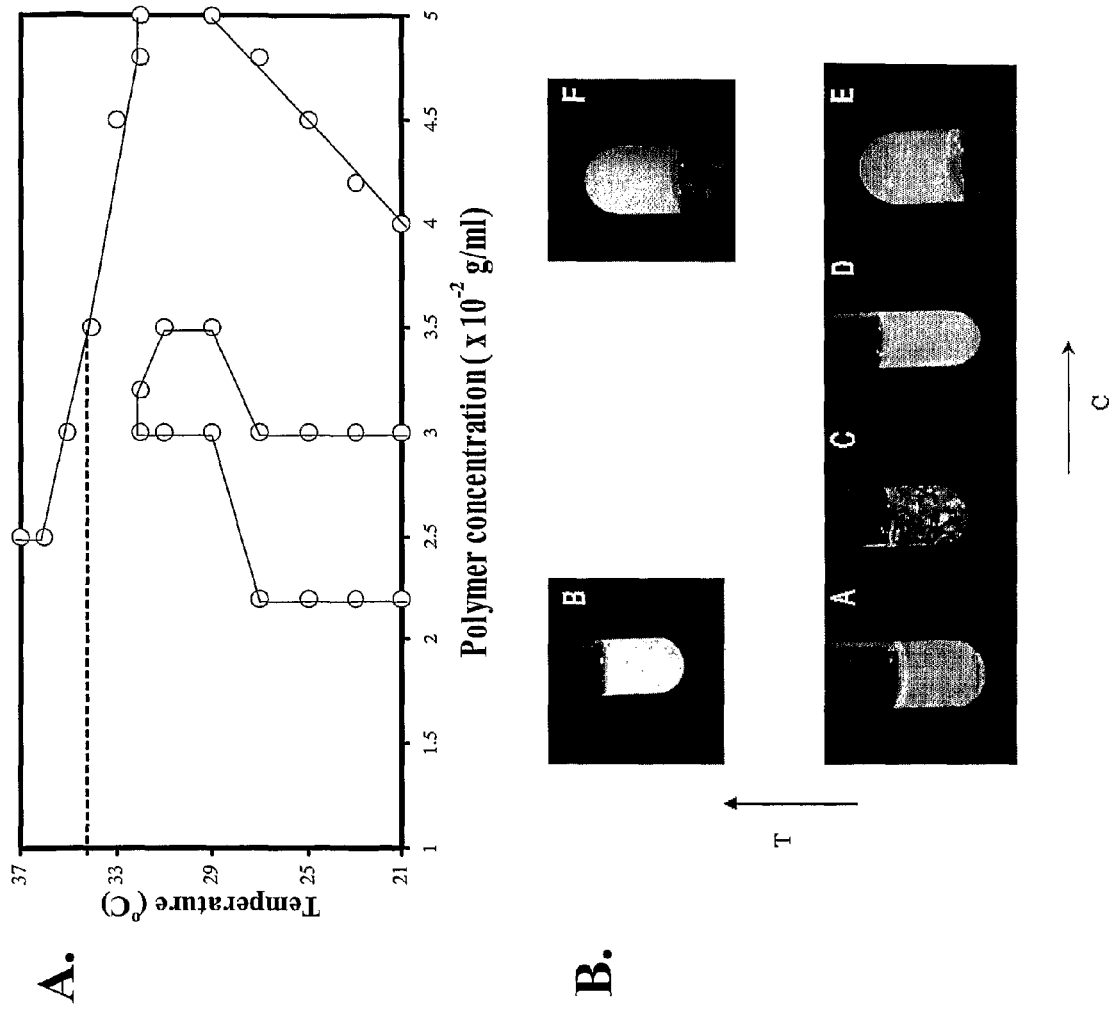
FIG. 9 shows the phase behavior of the PNIPAM-PAAc IPN nanoparticles in water. Panel A: The temperature-concentration phase diagram. There are six areas: (A) a homogeneous colloidal fluid, (B) a phase-separated colloidal fluid, (C) a colloidal crystal phase, (D) a colloidal glass, (E) a colloidal gel, and (F) a phase-separated colloidal gel. Panel B: shows representative black and white pictures of each phase: A) 1.0 wt %, 21° C., B) 1.0 wt %, 36° C., C) 2.5 wt %, 21° C., D) 3.5 wt %, 21° C., E) 4.5 wt %, 21° C., and F) 4.5 wt %, 36° C. The hydrodynamic radii of the PNIPAM and IPN particles at 20° C. are 125 nm and 155 nm, respectively and used for FIGS. 9-10, where the weight ratio of PNIPA to PAAc within the IPN particles is 2:1, determined by both an evaporation method and static light scattering.

2. Phase diagram of the semi-dilute IPN nanoparticle aqueous solution: The aqueous solutions of the IPN nanoparticles exhibit rich phase behavior as shown in FIG. 9($a$), determined by combining visual inspection, turbidity and viscosity measurements. The phase behavior has been divided into six areas with typical optical appearances as shown in FIG. 9($b$). At low polymer concentrations (<2.2×10$^{-2}$ g/ml, Area A), the IPN dispersions appear translucent and flow easily. The IPN nanoparticles are fully swollen. Upon increasing the temperature, the particle size shrinks and the dispersions enter into a phase-separated area (Area B). In the intermediate polymer concentration range (between 2.2 and 3.0×10$^{-2}$ g/ml, Area C), the IPN dispersions are colloidal crystal fluids at room temperature. These crystals are easy to observe due to their iridescent patterns caused by Bragg diffraction.[27] Iridescent color resulting from the Bragg diffraction of visible light by the periodic structure of bilayer membranes has been also reported before.[28] Constructive interference occurs if the Bragg condition, 2nd sin θ=mλ, is satisfied, where d, θ, n, λ, and m are the lattice spacing, the diffraction angle, the refractive index of the gel medium, the wavelength of light in vacuum and an integer, respectively. In a high polymer concentration range (between 3.0×10$^{-2}$ and 4.0×10$^{-2}$ g/ml, Area D), the IPN dispersions are colloidal glass fluids that are viscous fluids and exhibit a homogeneous color due to a short-range order.[26] At very high polymer concentrations (>4×10$^{-2}$ g/ml, area D) at room temperature, the IPN dispersions become colloidal gels. At higher temperatures, the gels become white and opaque (Area F).

The inverse thermoreversible gelation occurs in a broad polymer concentration above 2.5×10$^{-2}$ g/ml. That is, when the system is heated to above the gelation temperature $T_g$, it undergoes a transformation from a low-viscous fluid to a gel. This behavior is completely reversible.

The gelation of the IPN dispersion at T>$T_g$ may be caused by the attractive interactions between particles. At room temperature, PNIPAM particles are in the swollen state and they contain 97% water by volume. The van der Waals attraction between colloidal particles is negligible due to the close match in the Hamaker constants of the particle and the water.[29] The reduced osmotic second virial coefficient exhibits a sharp change at the volume transition temperature, beyond which it turns negative. Thermodynamic calculation indicates that the reduced interaction potential energy between nanoparticles increases by over six orders of magnitude as temperature changes from 24° C. to 36° C., with the sharpest increase near the volume transition temperature of 34° C.[29] The gelation may be achieved by the balance between van der Waal interaction between PNIPAM networks and the ionic repulsion of the PAAc networks in the IPN particles. It is noted that the temperature-dependent interparticle potential is also responsible to the formation of reversible or irreversible aggregates in colloidal systems of PNIPAM derivatives.[10] More convincing evidences are needed to determine the exact origin of the attractive force that bonds the IPN nanoparticles into a network at T>$T_g$.

Example 3

3. Controlled Drug Delivery from the In Situ Physically Crosslinked IPN Nanaoparticle Networks.

3.1. Drug loading and release from IPN nanoparticle networks: 0.5 g IPN nanoparticle semi-diluted aqueous dispersion was mixed with 0.025 g 4000 ppm dextran solution and shaken by an Fisher Vertex for 5 minutes at room temperature. The sample gelled immediately as the container vial was set in a 37° C. hot bath. The gel was kept its shape after it was pushed out from the vial by a long needle syringe. The drug release studies were carried out in 20 ml screw-capped glass vials. Each drug-loaded gel was put into a separate vial, to which was added 10 ml of phosphate buffered saline (pH=7.4) at 37° C. 0.5 ml of the solution was collected from the vials at different time intervals and the released drug was determined by a UV-Visible Spectrophotometer (Agilent 8453). The volume of the release medium in the vials was held constantly by pouring the sampling solution back after each measurement.

Figure 10:
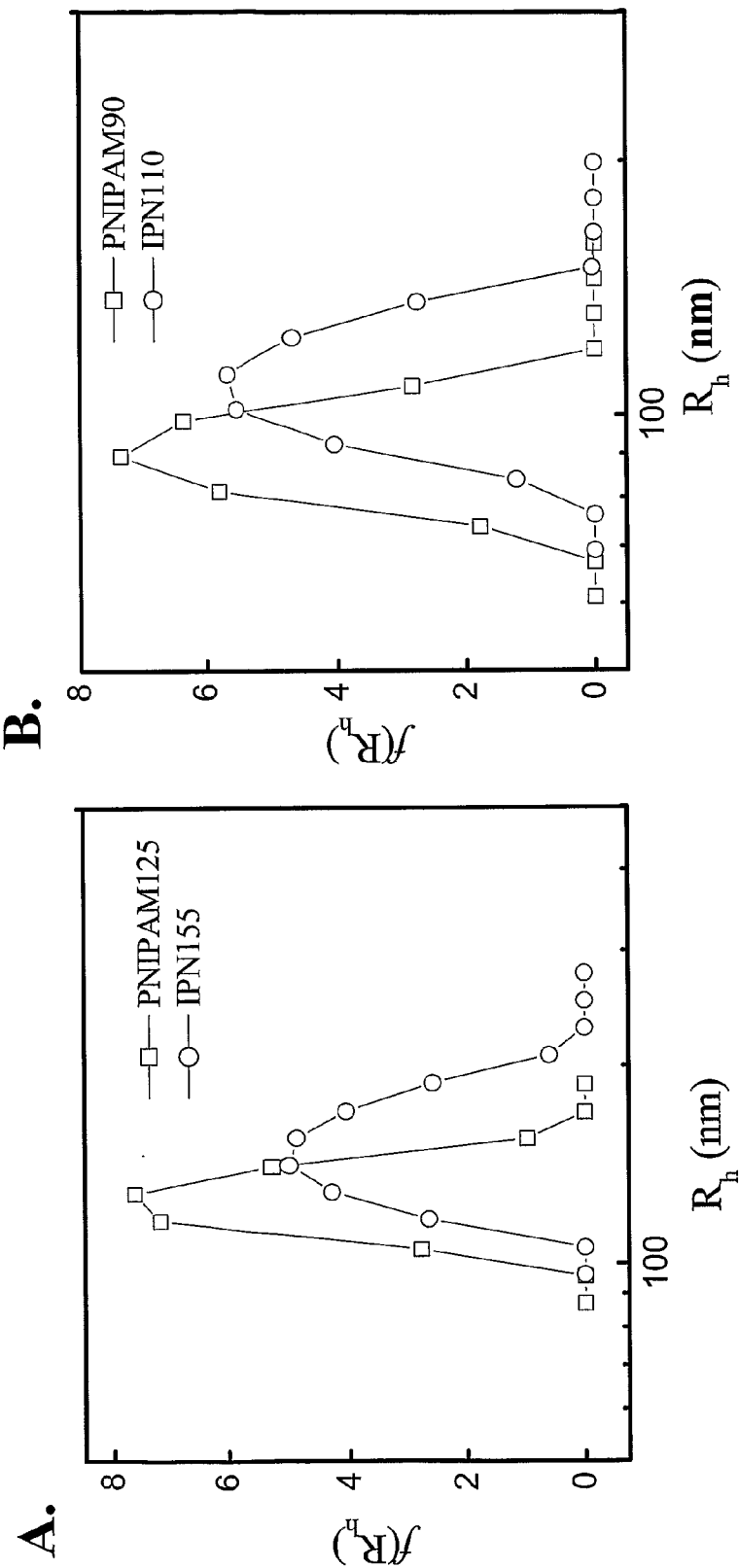
FIG. 10 shows the hydrodynamic radius distributions of IPN nanoparticles and their precursors PNIPAM nanoparticles in water at 23° C., measured by the dynamic light scattering method. (a) IPN155 and PNIPAM125 nanoparticles. (b) IPN110 and PNIPAM90 nanoparticles. Polymer concentrations and pH for both dispersions are adjusted, respectively, to $5.0 \times 10^{-5}$ g/ml and ca. 6.5-7.5.

3.2. Characterization of PNIPAM and IPN nanoparticles: Both PNIPAM and IPN samples were diluted to 5.0×10$^{-5}$ g/ml with distilled water and the pHs were adjusted to ca. 6.5-7.5 for dynamic light scattering characterization. The size distributions of IPN nanoparticle and its precursor PNIPAM nanoparticles are shown in FIG. 10. In FIG. 10($a$), the PNIPAM nanoparticles are narrowly distributed with $R_h$ around 125 nm and IPN were narrowly distributed around 155 nm. The calculated polydispersities (PD.I) for PNIPAM120 and IPN155 were 1.03 and 1.07, respectively. The weight ratio of PNIPAM to PAAc in each IPN nanoparticle is determined to be 1:0.50, using evaporation method. The smaller IPN nanoparticles was synthesized based on the smaller PNIPAM nanoparticles and their size distribution is shown in FIG. 10($b$), where the PNIPAM nanoparticles were narrowly distributed with $R_h$ around 90 nm and the IPN were distributed around 110 nm. The calculated polydispersities (PD.I) for PNIPAM90 and IPN110 were 1.05 and 1.08. The detailed comparison between IPN110 and IPN155 are listed in FIG. 27 (Table 2).

Figure 11:
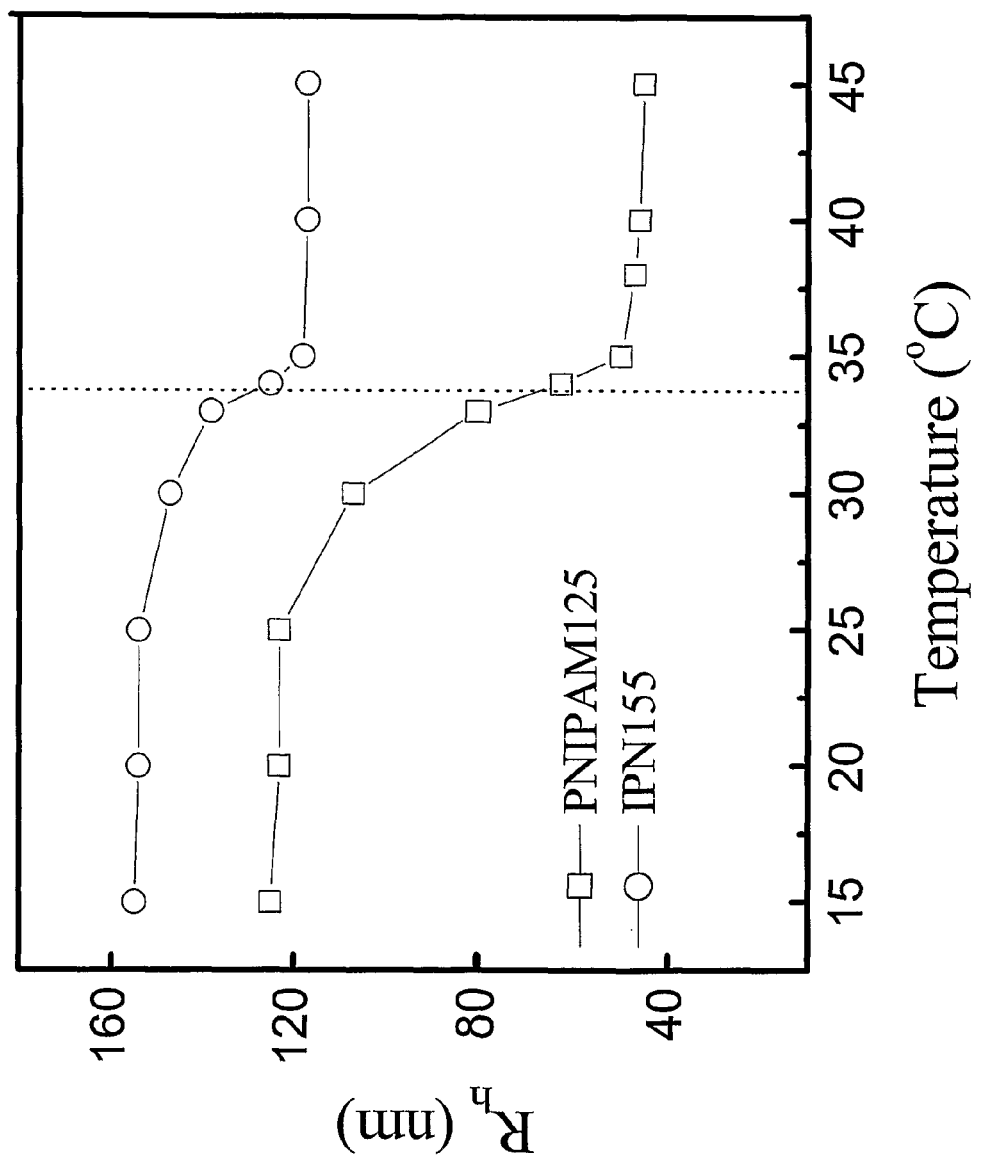
FIG. 11 shows the temperature-dependent particle sizes for PNIPAM125 nanoparticles and IPN155 nanoparticles in water. The polymer concentrations for both dispersions are $1.0 \times 10^{-5}$ g/ml. The dashed line indicates the volume phase transition temperature that is the same for both dispersions.

The hydrodynamic radius (Rh) variations of IPN and PNIPAM nanoparticles in diluted solution with polymer concentration of 1.0×10$^{-5}$ g/ml were measured by dynamic light scattering. As shown in FIG. 11, they undergo the drastic volume change at the same volume phase transition temperature of about 34° C. Specifically, the $R_h$ of PNIPAM nanoparticles shrank 64% from 125 nm to 45 nm at 34° C., while the $R_h$ value of the IPN nanoparticles decreased only 24% from 155 nm to 117 nm. The IPN formation may be understood in terms of the polymerization of acrylic acid within each PNIPAM microgel.[30-31] Although the PNIPAM microgels shrink slightly in acrylic acid solution due to an electrolyte effect, they swell enough at 21° C. (below LCST) allowing the acrylic acid monomer to diffuse into their interior. The interaction between the —COOH group on acrylic acid and the —CONH— group on PNIPAM, in the form of monomeric or dimeric hydrogen bonding, [32] causes the preferred growth of the PAAc network around the PNIPAM network. As the hydrophilic PAAc concentration gradually increases in the PNIPAM skeleton, the IPN particle swells more by absorbing more water.

3.3. Rheological properties of aqueous dispersions of IPN nanoparticles: Viscosity ($\eta$) is a fluid property that represents a materials internal resistance to deform, and defined as the ratio of shear stress ($\tau$) and shear rate ($\gamma$), i.e., $\eta=\tau/\gamma$. Here the temperature dependent viscosity of aqueous dispersions of IPN nanoparticles has been studied at various polymer concentrations. The viscosity was measured using a Brookfield viscometer with a shear rate of 100 rpm. In order to check the influence of the heating rate on the viscosity of the IPN and PNIPAM microgel dispersions, different heating rates varying between 1 and 5° C./5 mins were applied to the 3.27% IPN and PNIPAM samples. The various viscosity curves obtained were perfectly superimposed. This suggests that the associative phenomenon is rather fast and kinetic effects are unlikely. An intermediate heating rate value of 2° C./5 mins was utilized for the following examples.

Figure 12:
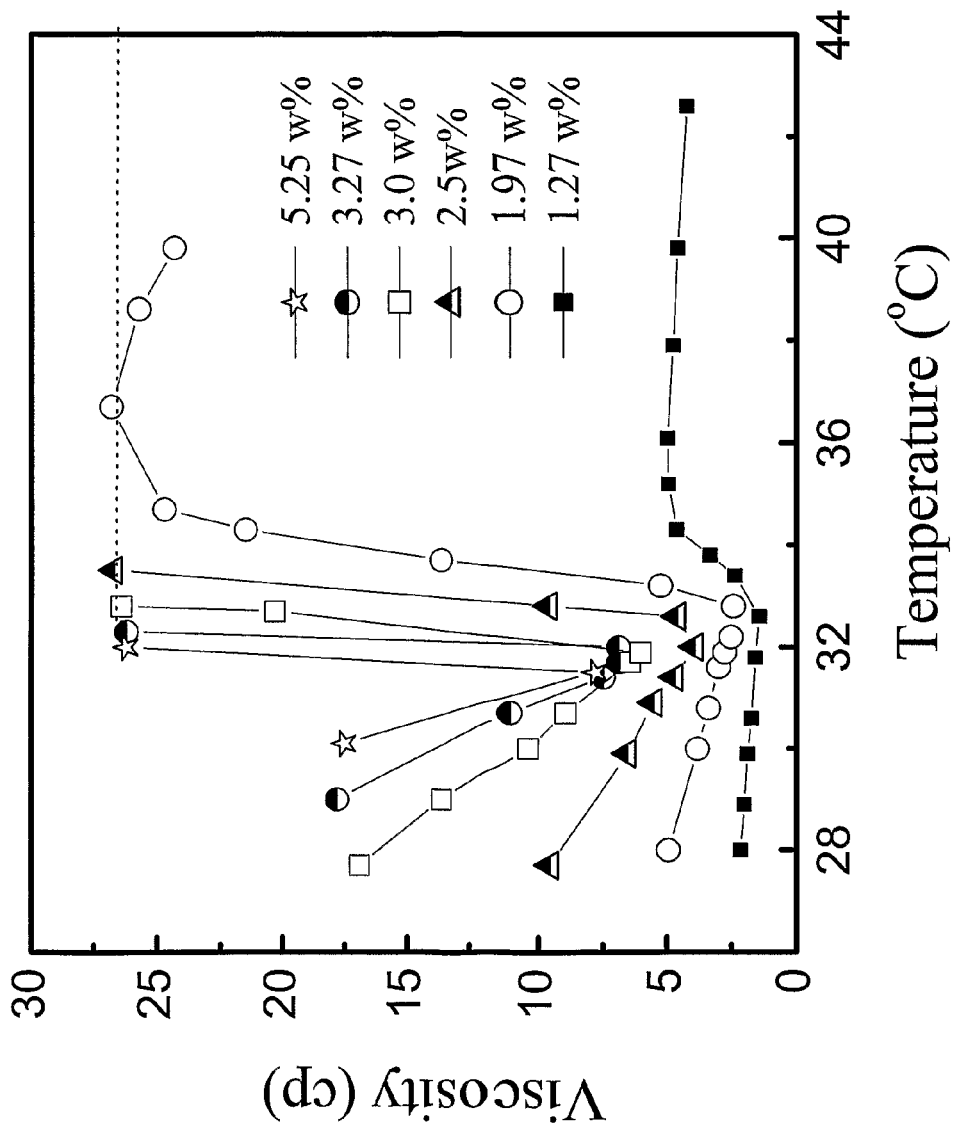
FIG. 12 shows the temperature dependent viscosity of aqueous dispersions of IPN155 nanoparticles at different polymer concentrations: 5.25 w %, 3.27 w %, 3.0 w %, 2.5 w %, 1.97 w % and 1.27 w %. The dash line is the maximum viscosity scale of the viscometer.

The viscosity was measured from a series of IPN155 nanoparticle water dispersions with polymer concentrations from 1.27 to 3.27 wt % as shown in FIG. 12. Before reaching the critical temperature ($T_c$) ca. ~33° C., viscosity for all the samples exhibits a continuous decrease upon increasing temperature. This viscosity decrease is caused by the shrinkage of the nanoparticle volume. The viscosity curves, however, turned upward at $T_c$ after showing a distinctive viscosity minimum at 7.85, 6.87, 6.02, 3.93, 2.43 and 1.44 cp for IPN155 nanoparticle solutions with polymer concentrations at 5.25, 3.27, 3.0%, 2.5%, 1.97 and 1.27 wt %, respectively. In contrast to the graft copolymer of PAAc-g-PNIPAM and other thermothickening systems [33], the semi-dilute IPN microgel aqueous dispersion experienced a rather abrupt viscosity enhancement instead of a graduate increase.

The IPN dispersion with a lower polymer concentration ($C<2.5\times10^{-2}$ g/ml) exhibits a viscosity enhancement but without gelling. For dispersions with higher polymer concentrations, the viscosity drastically increased and jumped beyond the viscometer's measurement range. Visual inspection revealed that the dispersion in the test tube was physically gelled and could not flow even the tube was set upside down. The gelation is caused by the attractive interactions between nanoparticles: the PNIPAM in each IPN nanoparticle provides physical crosslinking bonds between particles via a temperature-dependent interparticle potential, while PAAc in each IPN particle in the neutral pH provides ionic charges that are temperature-independent and prevent collapse of the particles into an aggregate.

3.4. Drug release from IPN nanoparticle network: Dextran markers of various molecular weights were used as model macromolecular drugs and mixed with an IPN nanoparticle dispersion. At room temperature, the dispersion is a viscous fluid and can be mixed with a dextran solution thoroughly. The drug-solution mixture was then heated to 37° C. at which point the dispersion became a gel. This gel was then taken out from the tube and immersed into a phosphate buffered saline (PBS) solution at 37° C.

Figure 13:
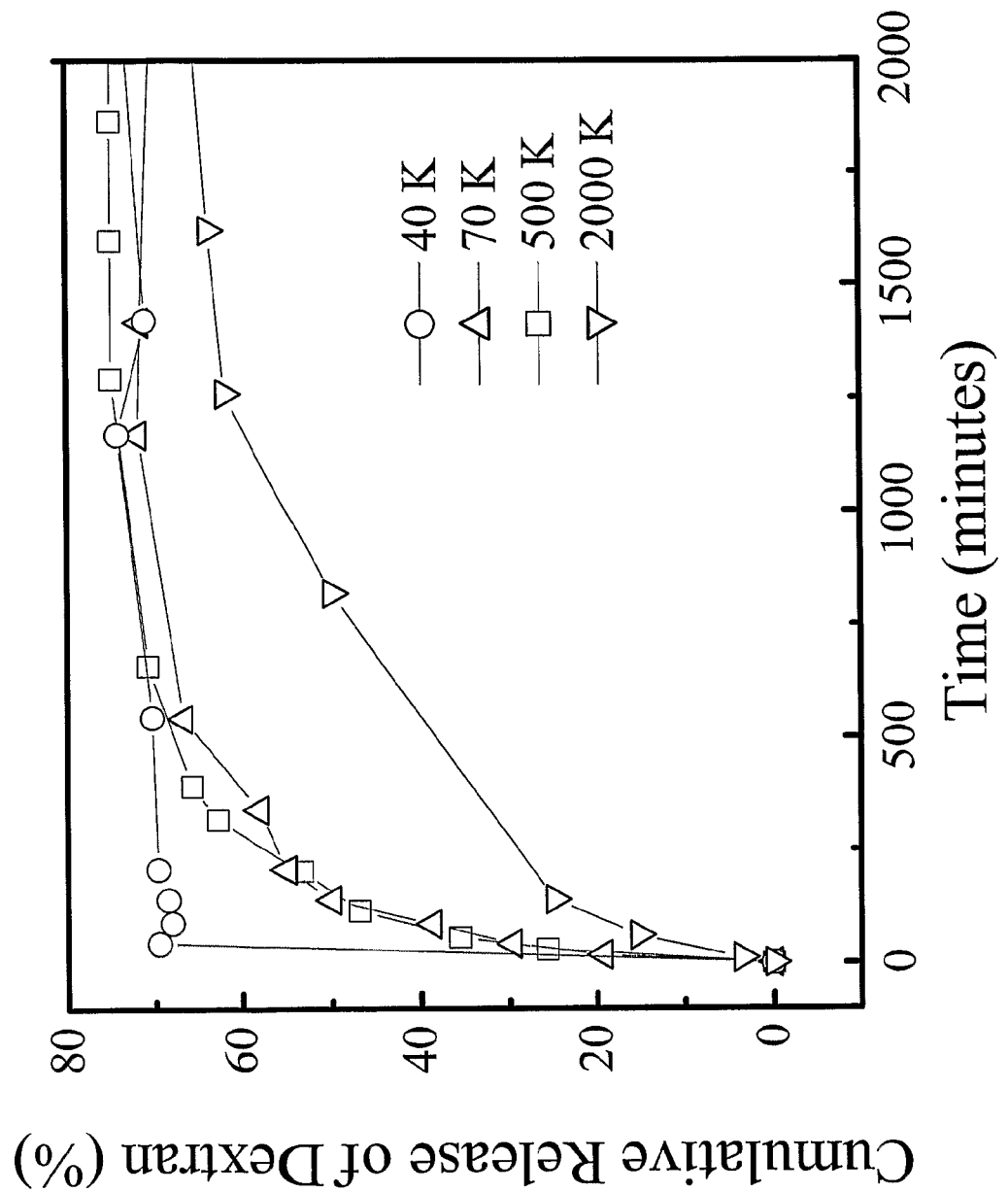
FIG. 13 shows the drug release profile from 5.25 w % IPN155 nanoparticle network in 50 mM phosphate buffered saline ("PBS") at pH 7.4 at 37° C. The dextran markers with different molecular weights of 40K, 70K, 500K and 2M were used as model macromolecule drugs. The weight ratio of PNIPAM to PAAc in each IPN nanoparticles is 1:0.50, as determined by the evaporation method.

The cumulative drug release from the IPN155 gel with particle radius of 155 nm and polymer concentration of 5.25 wt % was measured using a UV-Visible spectrophotometer as a function of time as shown in FIG. 13. It is clear that the molecules with smaller molecular weights diffuse out faster than those of higher molecular weights. The release rates slowed down gradually for 500K and 2M drug analogs in the order of their molecular weights. The drug molecules here were entrapped between IPN nanoparticles, permitting the release of molecules with very large molecular weight of 2M. It is noted that the polymer concentration used in the release experiment is about 4 times smaller than that used in a polymer solution system.[34]

Figure 14:
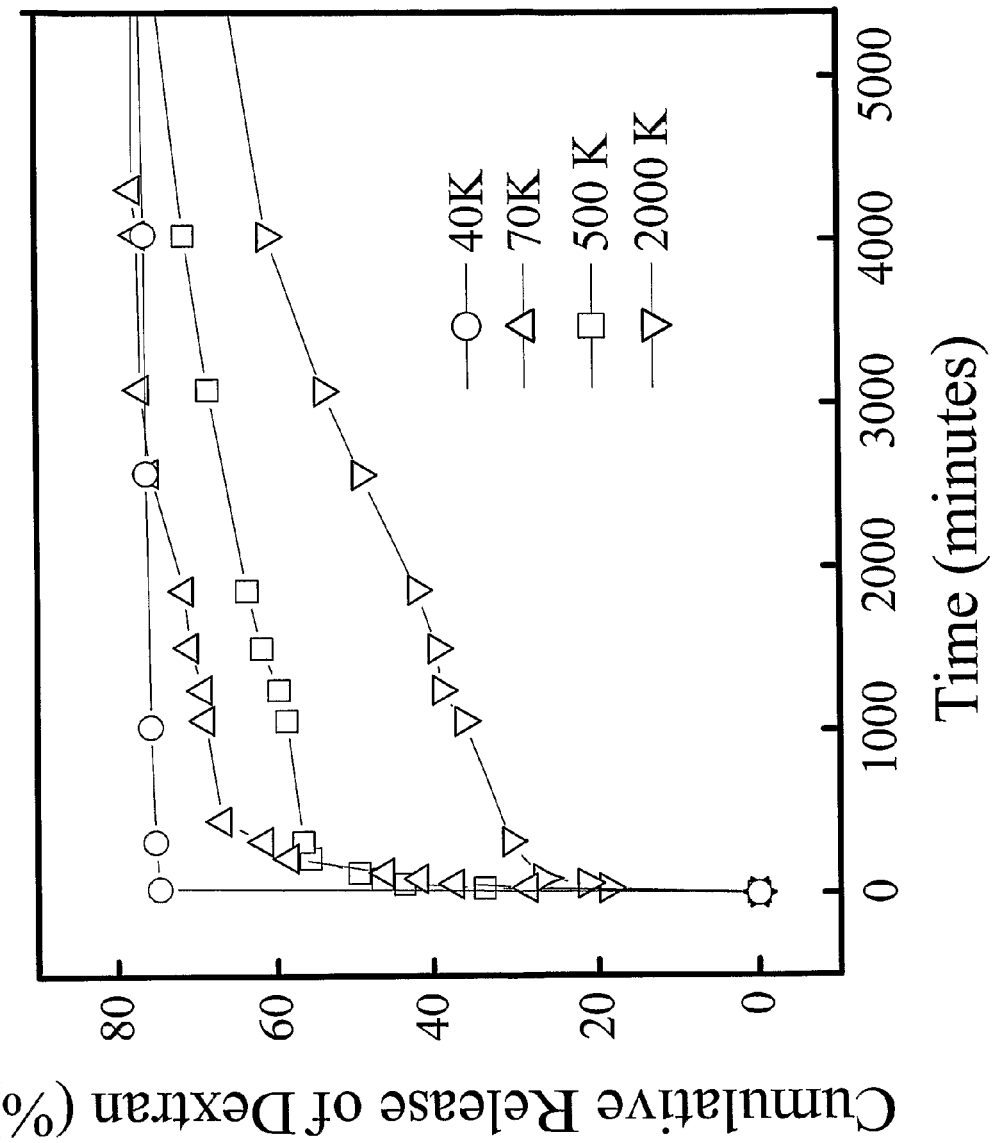
FIG. 14 shows the drug release profile from 5.25 w % IPN110 nanoparticle network in 50 mM phosphate buffered saline ("PBS") at pH 7.4 at 37° C. The dextran markers with different molecular weights of 40K, 70K, 500K and 2M were used as model macromolecule drugs. The weight ratio of PNIPAM to PAAc in each IPN nanoparticle is 1:0.13.

The effect of the nanoparticle size on the drug release rate was investigated. Following the same procedures of the above experiment, the release profiles for the IPN gel that has a smaller particle radius (110 nm instead of 155 nm) but the same polymer concentration (5.25 wt %) were measured, as shown in FIG. 14. Comparing FIGS. 13 and 14, one can see that decreasing the particle radius from 155 nm to 110 nm does not have a significant influence on the release of molecules with molecular weight smaller than 500 K but does affect molecules with larger molecular weight such as blue dextran. Using the time at which the released drug reaches 60% of the total load of 10 ppm as a characterized time ($\tau$), the nanoparticle gel with the smaller size were found to have an impact on the release of larger molecules (2M blue dextran): $\tau=4000$ min for IPN110 gel while $\tau=1300$ min for IPN155 gel. The slower release for the IPN110 gel is because the interparticle space is smaller in comparison with the one for the IPN155 gel.

Figure 15:
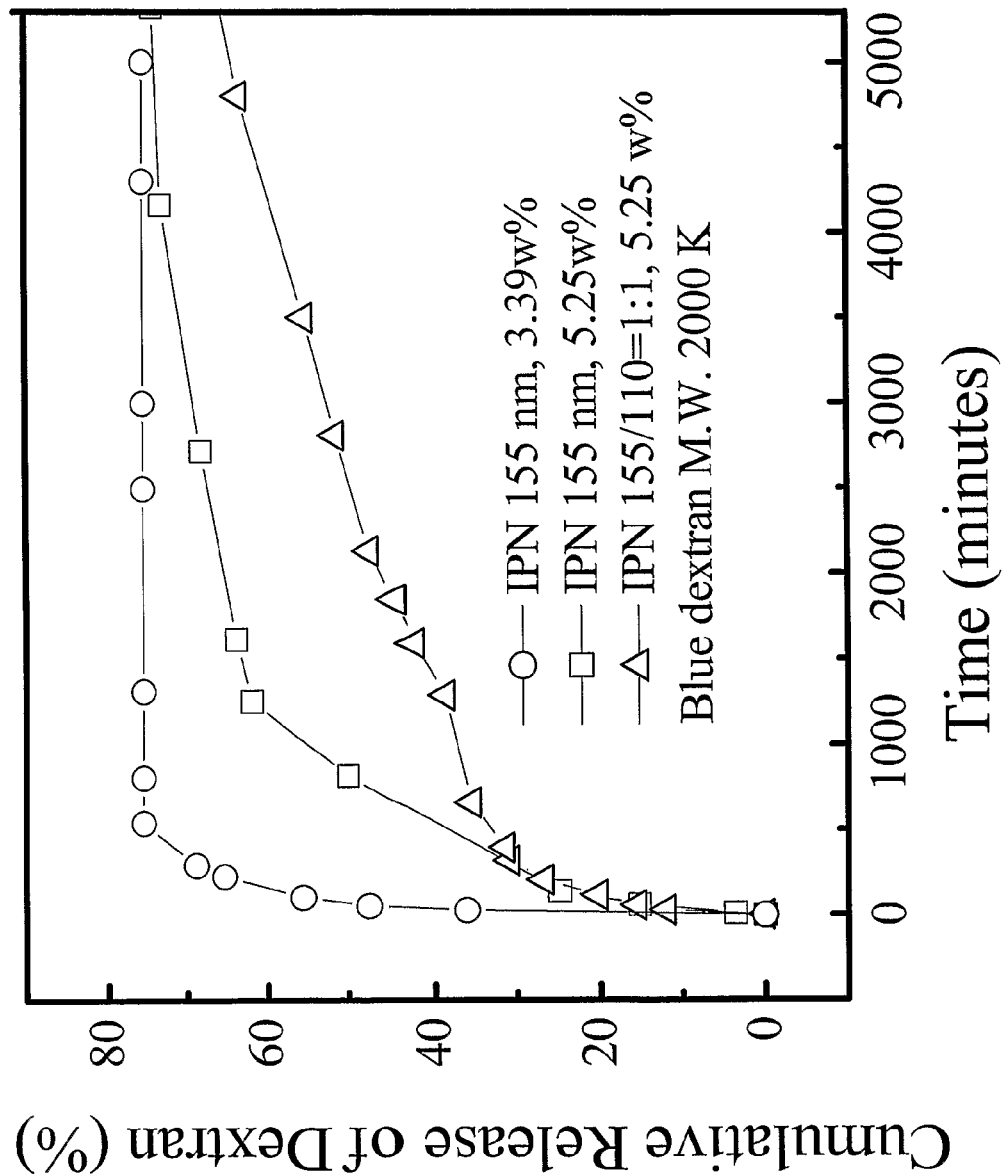
FIG. 15 shows the release profiles of blue dextran (MW 2 M) from 3.39 w % and 5.25 w % IPN155 nanoparticle networks, and 5.25 wt % IPN155-IPN110 (1:1) mixed nanoparticle network.
Figure 16:
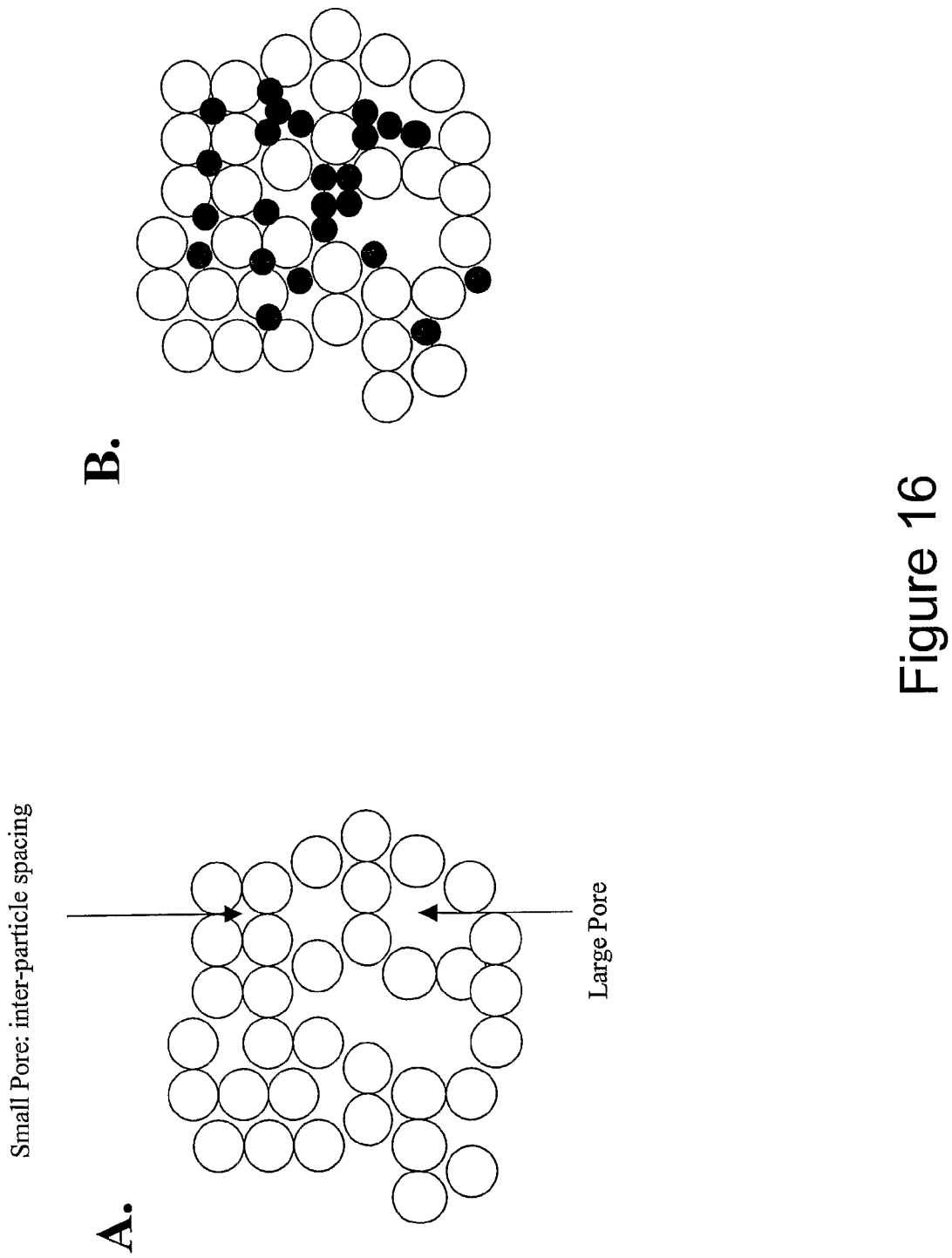
FIG. 16 shows the schematic diagram of the physically bonded nanoparticle network that is formed above the gelation temperature. (a) There are small sized pores with the size determined by interparticle spacing and the large sized pores with the size determined by the number of surrounding particles. (b) The nanoparticle network formed by mixing small and large particles. The small particles can fill in either the interstitials between particles or large pores, slowing down the release of drug molecules.

To examine how the IPN concentration affects the drug release rate, the blue dextran release from the nanoparticle networks formed by 3.29 w % and 5.25 w % IPN155 nanoparticle solutions were compared, respectively, as shown in FIG. 15. Again, using the time at which the released drug reaches 60% of the total load of 10 ppm as a characterized time ($\tau$), $\tau=200$ min for 3.29 w % gel, while $\tau=1300$ min for the 5.25 wt % gel. This is caused by the formation of large pores in 3.29 wt % nanoparticle network due to less available nanoparticles as building blocks. Most of the blue dextrans are therefore entrapped in such large pores, leading to the fast release rate. There may be two types of pores created during the formation of an IPN nanoparticle network: one is large and encircled by many nanoparticles; the other is small and encircled by compact nearest neighboring particles as shown in FIG. 16a. The size of the large pores is determined by the number of surrounding particles. Upon the decrease of the polymer concentration, both the size and the number of the large pores increases. On the other hand, the size of the small pore is determined only by the particle size: the bigger the spherical building block, the larger the inter-particle pore. The initial burst release is due to the drug entrapped in the large pores while the slow, late release is due to the drug entrapped in the small pores. The characterized time ($\tau$) required for 60% of the loading drugs being released from IPN microgel networks at 37° C. are listed in FIG. 28 (Table 3). Electronic or optical images of "pores" were not obtained, however, the schematic diagram in FIG. 16 is based on the understanding of drug releasing profiles.

Figure 17:
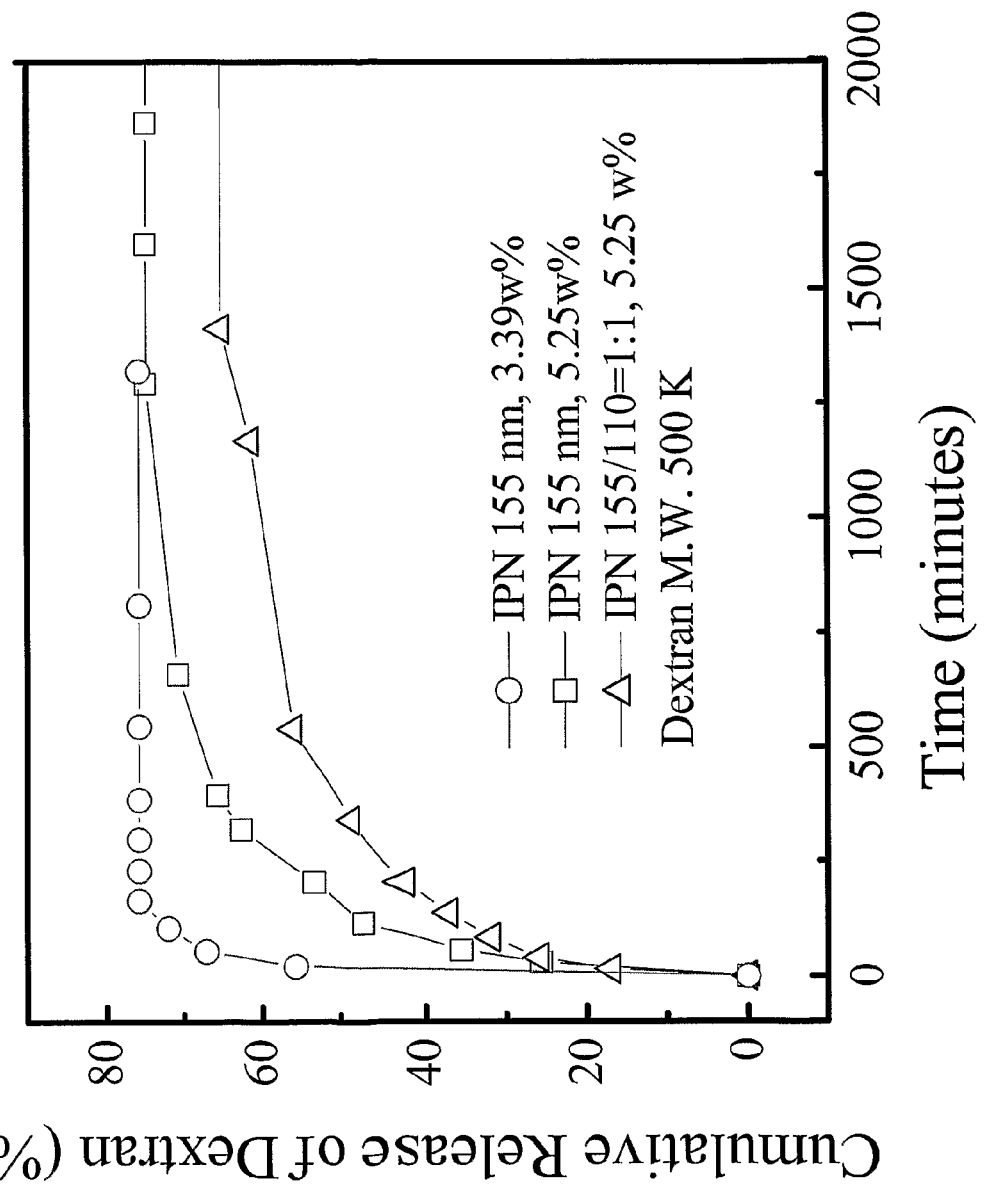
FIG. 17 shows the release profiles of Dextran Marker (MW. $5.0 \times 10^5$) from 3.39 w % and 5.25 w % IPN155 nanoparticle network, and 5.25 w % IPN155-IPN110 (1:1) mixed nanoparticle network in 50 mM PBS at 37° C.

One strategy to decrease such inter-particle pore size is to use small nanoparticles to fill into the inter-particle pores created by the large nanoparticles. To test the effectiveness of this approach, a mixture of IPN155 and IPN110 solution with weight ratio of 1:1 was prepared, the total concentration of IPN was kept at 5.25 w %. The release profile of blue dextran from this IPN155/IPN110 mixed nanoparticle network is compared with that from IPN155 nanoparticle network. The characterized time for the released drug reaches the 60% of the total load for IPN155/IPN110 gel is about 4600 min, much longer than 1300 min required for the IPN155 gel. The same experiment as described in FIG. 15 was also repeated for a dextran with molecular weight of 500 K. Similar results have been obtained as shown in FIG. 17. This suggests that using small particles to fill in the pores in the larger particle network is an effective method to reduce the release rate (FIG. 16b).

Figure 18:
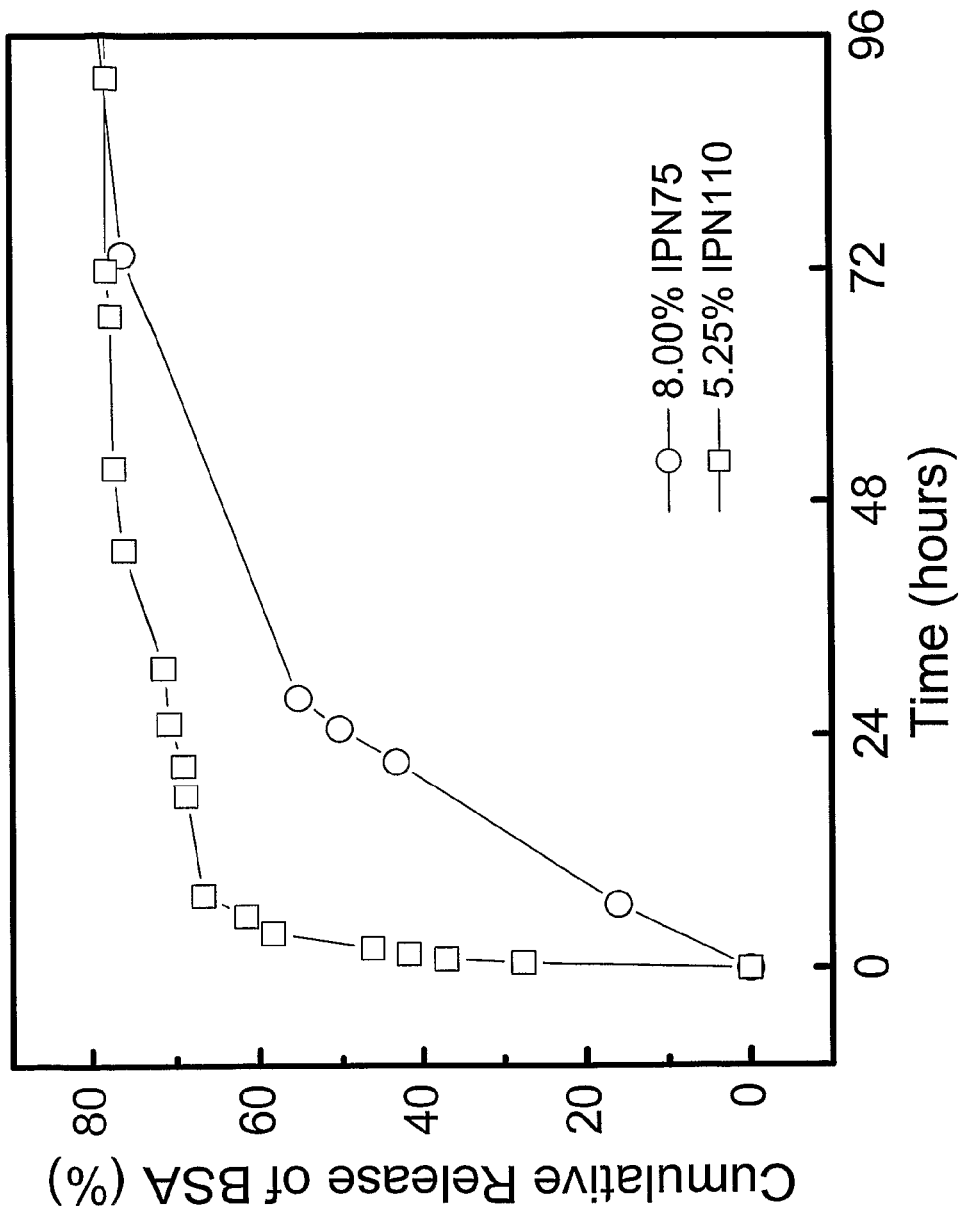
FIG. 18 shows the cumulative release of BSA (M.W. 67 k) from 8 wt % 75 nm IPN nanoparticle networks V.S. the release of dextran (M.W. 70 k) from 5.25% 110 nm IPN nanoparticle networks at 37° C. in PBS.

The bovine serum albumin (BSA) as a model protein drug was also loaded into the IPN nanoparticle networks. The slow release rate was achieved by using higher polymer concentration (8 wt %) of the network and smaller sized nanoparticles ($R_h$=75 nm) as shown in FIG. 18. Drug partitioning and swelling behavior in thermal responsive gels have been investigated before. [20, 35-36] It will be an interesting experiment to extend these studies to the current system.

Example 4

4. Synthesis of the Soft Nano-clusters Composed of the IPN Nanoparticles Building Blocks:

4.1. Nanoclusters synthesis: first, IPN nanoparticle was prepared as described in 1.3, where the second step interpenetrating reaction temperature was regulated at 23° C. with water bath. The $R_h$ of the resultant IPN microgel in neutral pH environment is 155 nm, measured by dynamic light scattering. The IPN microgel was then treat by dialysis and ultracentrifuge and the final polymer content was adjusted to be 2.90 w %. 0.1 gram of this IPN solution was diluted to 10 ml with distilled water in a cylindrical test vial. 0.01 gram 1-ethyl-3-(3-dimethlyaminopropyl)carbodiimide hydrochloride (EDAC) and 0.01 gram Adipic acid dihydrazide, as crosslinking agents, were dissolved in 10 ml water and added to the IPN solution. The mixed solution was then set in (44±1)° C. hot bath. After the first 30 minutes, 0.1 ml aliquots were taken from the test vial every 5 minutes until the precipitates occurred.

Figure 19:
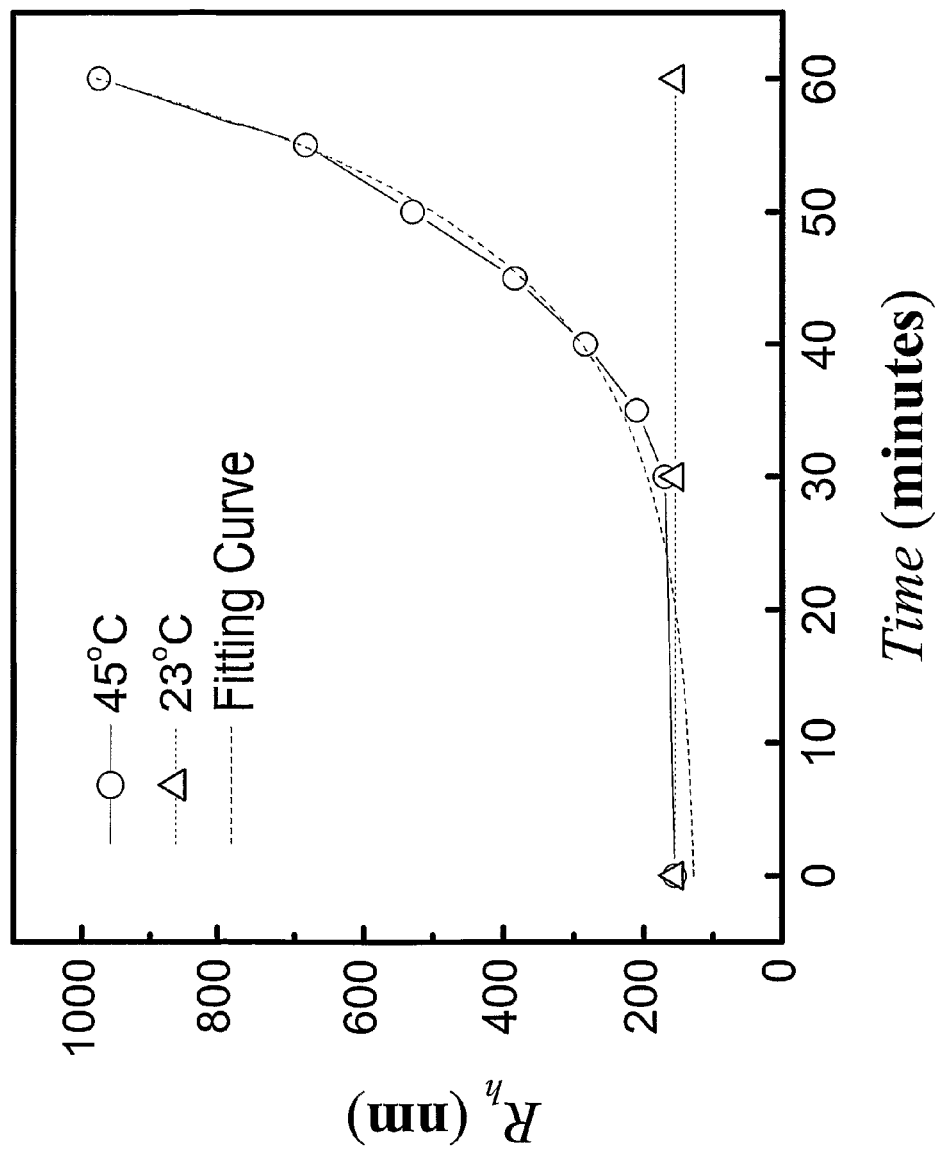
FIG. 19 shows the variation of the particles hydrodynamic radius ($R_h$) against reaction time in the process of pomegranate microgel formation. Here 0.1 mL aliquots of solution were taken from the reaction container at the different reaction times for dynamic light scattering analysis. The concentrations of all samples for DLS are $5.0 \times 10^{-6}$ g/ml, on the basis of IPN microgel solid content. The pH values were adjusted between 6.5 and 7.0.

4.2. Reaction kinetics of the nanocluster formation. As illustrated in 1.7, the semi-diluted solution (2.5 wt % or above) of IPN microgels composing PAAc and thermo-sensitive PNIPA exhibited strong inter-particles hydrophobic interactions and were capable to reversibly form a physical bonded nanoparticle networks when the solution being heated to above 34° C. Similarly, stronger interactions and more frequent collisions between IPN microgels are expected in dilute solution upon raising temperature. In this work, a certain number of IPN microgels are chemically bonded through the carboxyl groups of PAAc in the process of IPN nanoparticles collision. The kinetics of the nanoclusters formation was studied by measuring the hydrodynamic radius ($R_h$) change of the particles as a function of reaction time. Here 0.1 ml of aliquot solution was taken from the reaction container at different reaction times, and diluted to $5 \times 10^{-6}$ g/ml with distilled water for dynamic light scattering analysis. As shown in the FIG. 19, the IPN microgels have an average $R_h$ of 155 nm at 21° C. before the reaction. The inter-particles crosslinking was initiated by adding 1-ethyl-3-(3-dimethlyaminopropyl)carbodiimide hydrochloride (EDAC) and adipic acid dihydrazide at 44° C. It's found that the particle size increases little during the first 30 minutes, but dramatically in the following 30 minutes. Further reaction for 10 more minutes lead to the precipitates. The data are well described by an equation of $R_h = 155 + 6.38 e^{t/\tau}$, where the characterization time $\tau$=12 min. Visual observation revealed that the solution turned from blurred blue to white and finally to precipitation during the nanocluster growth. To study the effect of temperature, same reaction was carried out at 23° C. There is no particle size change being observed for more than one week, which indicates that strong particle-particle interaction and frequent collision are preliminary conditions for this type of nanocluster formation.

Figure 20:
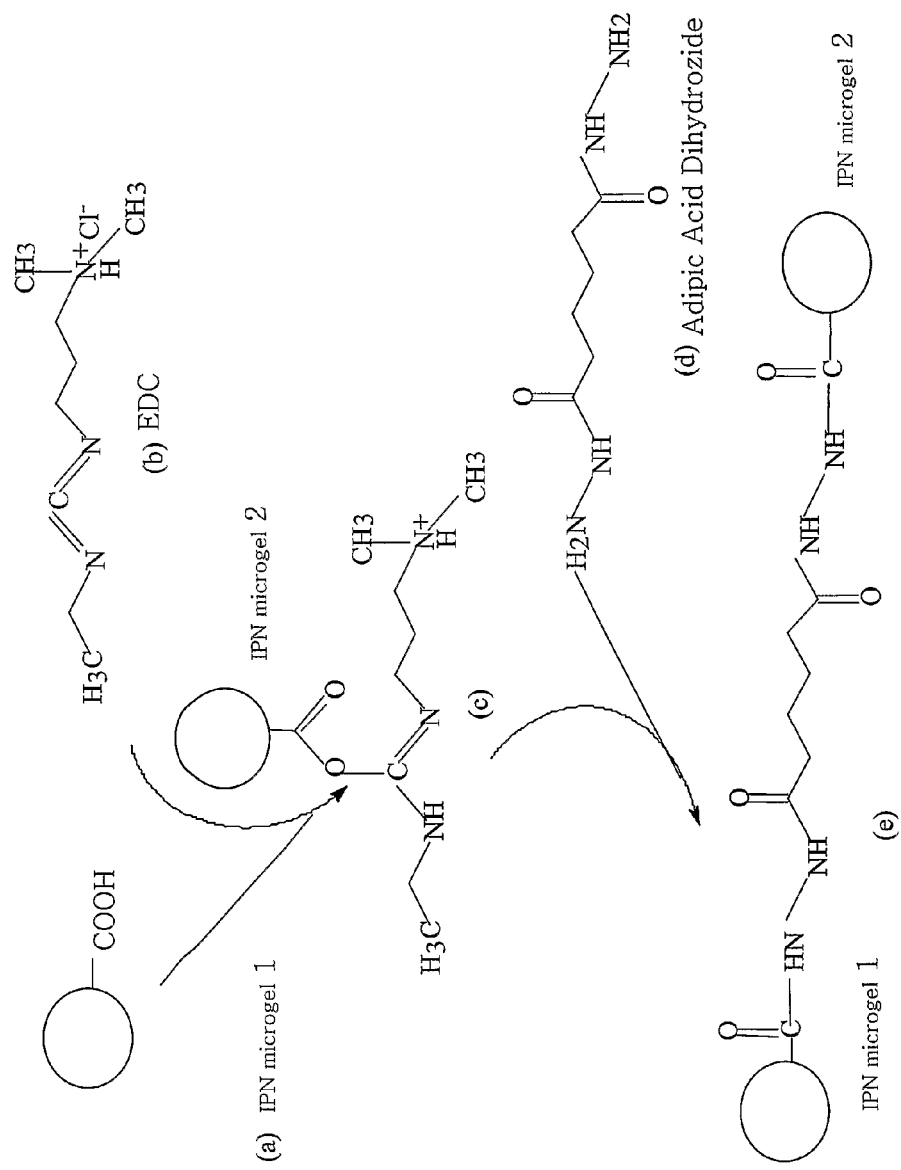
FIG. 20 shows the soft nanoclusters synthesis scheme, where IPN microgel building blocks are zero distance crosslinked by EDAC and adipic acid dihydrazide through the carboxyl-amine reactions.

The crosslinking mechanism between IPN microgels is schematically drawn in FIG. 20, where 1-ethyl-3-(3-dimethlyaminopropyl)carbodiimide hydrochloride (EDC) and Adipic acid dihydrazide are commonly used crosslinking reagents for carboxyl groups [CarbodiiGreg T. Hermanson, Bioconjugate Techniques, 1996 by Academic Press, San Diego, Calif.]. N-substituted carbodiimides of EDC (b) can react with carboxylic acids on IPN microgel (a) to form highly reactive O-acylisourea derivatives (c) that are extremely short-lived. This active species then react with two ends primary amines of adipic acid dihyrazide (d), resulting in the neighboring IPN microgels being chemically crosslinked (e). In order to fabricate monodisperse nanopomegranate in a controllable manner, it is necessary to disperse the building block IPN microgels in a dilute solution to avoid the formation of large IPN microgels aggregates or networks. On the other hand, a strong particle-particle interaction is desirable when the reaction starts. In dilute condition, the interactions between IPN microgels are very weak at room temperature thus no reaction was observed. Upon raising temperature to 44° C. (above the LCST of PNIPA), there is a stronger inter-particle attraction because of the phase transition of PNIPA in each IPN microgel. The large amount of carboxyl groups and the well-separated distance between IPN microgels in dilute solution, as well as the sensitivity of IPN microgels to temperature, allow the nanoclusters to grow in a controllable manner.

Figure 21:
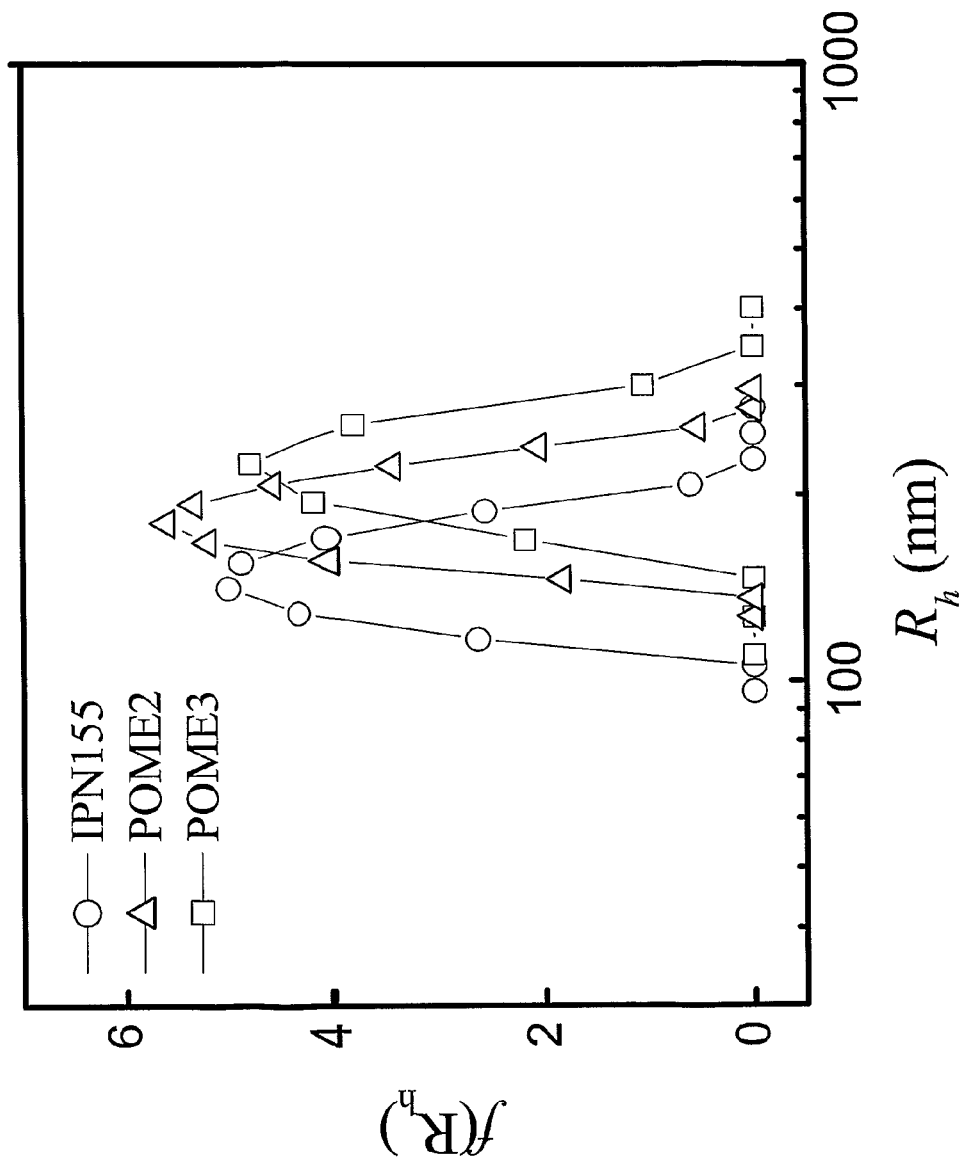
FIG. 21 shows the particle size distributions of the pomegranate microgels and building block IPN microgels at 21° C., where IPN155, Nanocluster2 and Nanocluster3 stand for PNIPAM/PAAc interpenetrating polymer network microgel, dimmer (195 nm for 33 mins) and triplet (235 nm for 37 mins), respectively. The measuring angles of dynamic light scattering are 30° for all.

4.3. Comparison of IPN microgels and nanoclusters at 21° C. Nanoclusters were characterized by both dynamic and static light scattering and compared with their building block IPN particles studied previously. Both nanoclusters and IPN nanoparticles were diluted to $5.0 \times 10^{-6}$ g/ml with distilled water with pH 6.5-7.0. The particles size and distribution are shown in FIG. 21, where the IPN microgels are narrowly distributed with $R_h$ around 155 nm. Cluster2 and Cluster3 refer to the IPN microgels dimmers and triplets, which were synthesized by lasting the particle-particle crosslinking for 33 and 37 minutes, respectively. According to the relationship between particle hydrodynamic radius $R_h$ and their molecular weight Mw $4/3 * \pi R_h^3 \rho = M_w/N_A$, the dimmer of 155 nm IPN particle should have the $R_h$ around $155 \times 2^{1/3} = 195$ nm and the triplet should have the $R_h$ around $155 \times 3^{1/3} = 223$ nm. In FIG. 21, Cluster2 and Cluster3 have the $R_h$ of 195 nm and 235 nm, respectively and therefore it is reasonable to statistically consider them as IPN microgel dimmers and triplets. The calculated polydispersity index (PD.I) for IPN, Cluster2 and Cluster3 are all around 1.07. Increased particle size and their narrow distribution demonstrate that nanoclusters are growing in a controllable manner.

Figure 22:
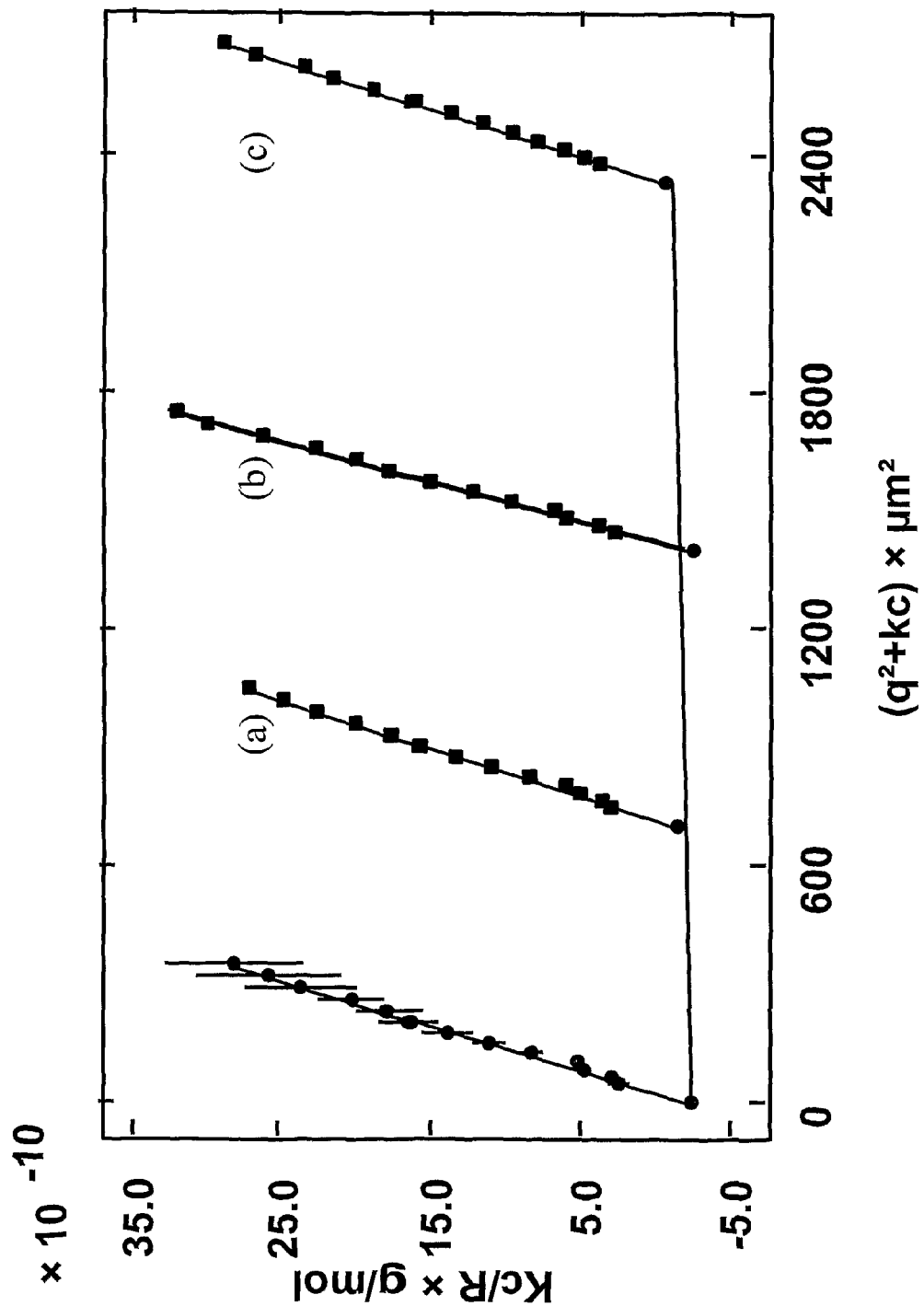
FIG. 22 shows the Zimm plots of static light scattering for Nanocluster3 microgel at 21° C. The polymer concentrations are (a) $2.5 \times 10^{-6}$ g/mL, (b) $5.0 \times 10^{-6}$ g/mL, (c) $7.5 \times 10^{-6}$ g/mL, respectively.
Figure 23:
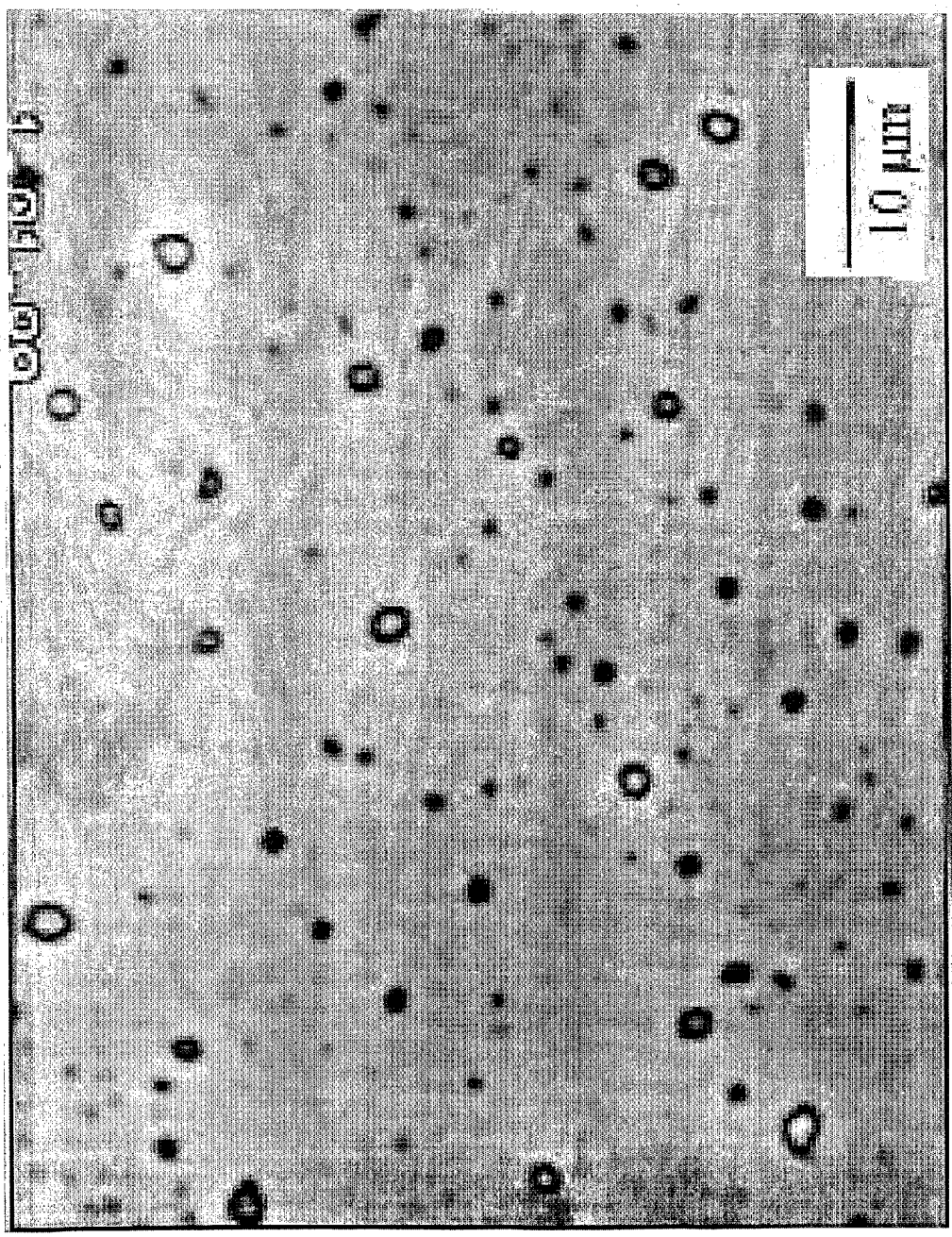
FIG. 23 shows the image of the micrometer scale cluster particles observed by optical microscope.
Figure 24:
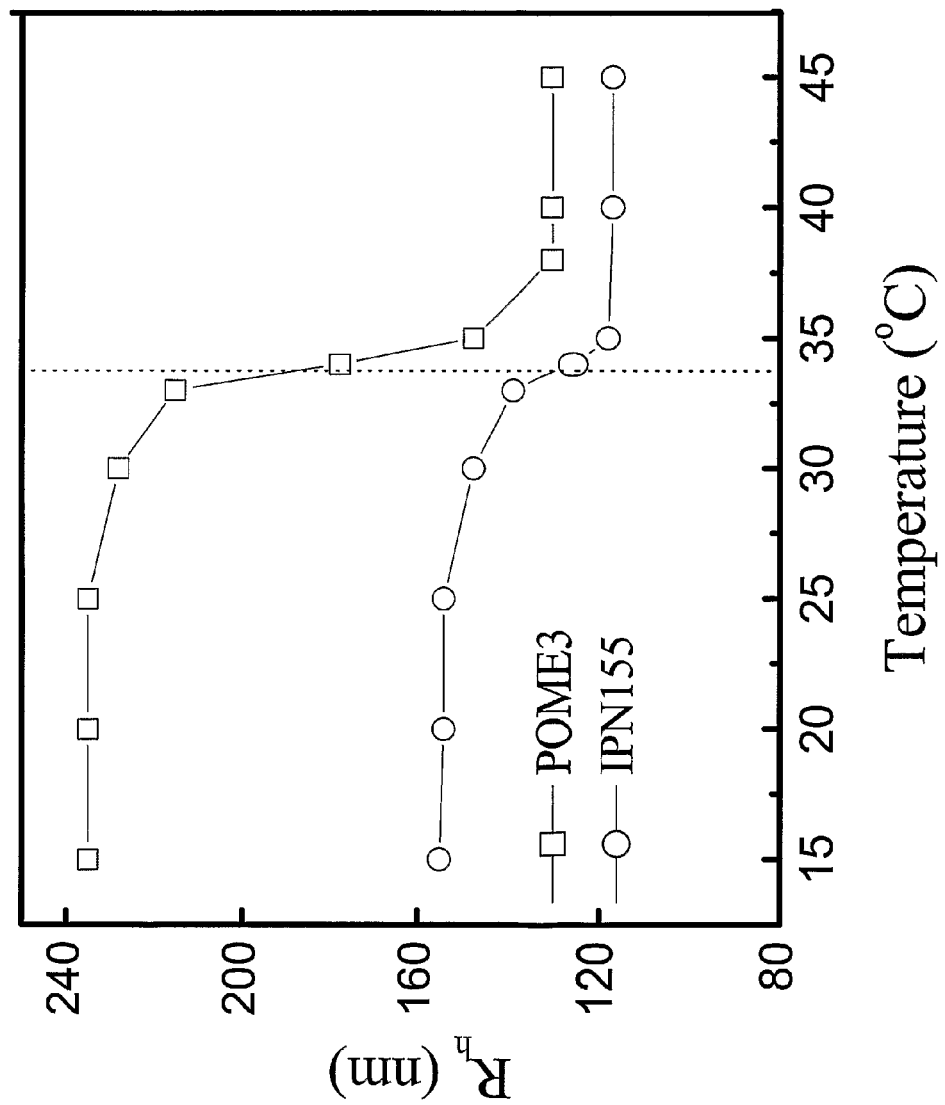
FIG. 24 shows the temperature sensitivity of the nanoclusters.

FIG. 22 shows the Zimm plot for the pure Cluster3 aqueous solution at 21° C., with sample concentration varying from $2.5 \times 10^{-6}$ g/ml to $7.5 \times 10^{-6}$ g/ml. The value of dn/dc used here is 0.102 cm$^3$/g, measured by a refractometer. From the extrapolation of $KC/R_{vv}(q)$ in Eq. 1 to the zero angle and zero concentration, the molar mass $M_w$ and the radius of gyration $<R_g>$ are determined to be $9.3 \times 10^9$ g/mol and 178 nm, respectively. By combining DLS and SLS results, the ratio of $<R_g>/<R_h>$ was found to be 0.75, which is close to the theoretical value of $(3/5)^{1/2}$ for a uniform hard sphere. The density of a Cluster3 ($\rho$) in water is estimated about $1.36 \times 10^{-2}$ g/cm$^3$ at 25° C. in water using the equation $4/3 * \pi R_h^3 \rho = M_w/N_A$, where $R_h$ and $M_w$ are obtained from DLS and SLS, respectively, and $N_A$ is Avogadro's number. The detailed comparison between Cluster3 and IPN microgels is listed in FIG. 29 (Table 4), where both molecular weight and particle size $R_h$ demonstrate Cluster3 is IPN microgel triplets. If the reaction lasted longer, the pomegranate weight will increase accordingly and become Cluster4, 5 and so on, and eventually become micrometer scale precipitates as shown in FIG. 23.

4.4. Temperature induced volume phase transition. The nanocluster undergoes the volume phase transition at 33° C. that is the same as the one for the IPN microgel. The volumes changes of the Cluster3 and its building block 155 nm IPN microgel are shown in FIG. 6 as a function of temperature.

FIG. 6 is shown in black and white and indicates the viscosity change of the IPN semi-dilute aqueous solution with polymer concentration of $2.5 \times 10^{-2}$ g/ml. Below ~34° C., the dispersion is a fluid and above ~34° C., the dispersion becomes a solid. The color of the dispersion is due to the Bragg diffraction from an ordered array of colloidal particles in water. The $R_h$ of IPN microgel shrank about 24% from 155 nm to 117 nm, whereas Cluster3 shrank about 45% from 235 nm to 129 nm upon raising temperature. The enhanced deswell ability of Cluster3 indicates the collapsing force of the triplet involves not only the individual IPN microgel shrinkage but also a stronger inter-particles PNIPA collapse within the nanoclusters. No obvious pH sensitivity is observed for Cluster3 particles since the majority of the carboxyl groups are consumed during crosslinking.

The principles to design and the processes to fabricate other hydrogel nano/micro-particles dispersions possessing the similar inverse thermoreversible gelation behavior will be apparent to those of ordinary skill. While the compositions and methods of this invention have described in terms of preferred embodiments, it will be apparent to those of skill in the art that variations may be applied to the composition, methods, periods of time, and in the steps or in the sequence of steps of the method described herein without departing from the concept, spirit and scope of the invention. More specifically, it will be apparent that certain agents that are both chemically and physiologically related might be substituted for the agents described herein while the same or similar results would be achieved. An industrial scaling of the methods disclosed herein are understood to be within the spirit and scope of the invention. All such similar substitutes and modifications to those skilled in the art are deemed to be within the spirit, scope and concept of the invention as defined by the appended claims.

REFERENCES CITED

The following references, to the extent that they provide exemplary procedural or other details supplementary to those set forth herein, are specifically incorporated herein by reference.

U.S. Patent Documents

U.S. Pat. No. 6,749,868 issued to Desai, et al., on Jun. 15, 2004, titled "Protein Stabilized Pharmacologically Active Agents, Methods for the Preparation Thereof and Methods for the Use Thereof."

U.S. Pat. No. 6,639,014 issued to Pathak, et al., on Oct. 28, 2003, titled "Multiblock Biodegradable Hydrogels for Drug Delivery and Tissue Treatment."

U.S. Pat. No. 6,632,457 issued to Sawhney on Oct. 14, 2003, titled "Composite Hydrogel Drug Delivery Systems."

U.S. Pat. No. 5,403,893 issued to Tanaka, et al., on Apr. 4, 1995, titled "Interpenetrating-Polymer Network Phase-Transition Gels."

Other Reference:s

Ilmain, F., Tanaka, T., Kokufuta, E. *Nature* (London, United Kingdom) 1991, 349, 400-1.

Sperling, L. H. *Adv. Chem. Ser.* 1994, 239, 12.

Wang, C. J., Hu, Z. B., Chen, Y. Y., Li, Y. *Macromolecules* 1999, 32, 1822-1827

Chen, L., Gong, J., Osada, Y. *Macromolecular Rapid Communications* 2002, 23(3), 171-174.

Katono, H., Sanui, K., Ogata, N., Okano, T., Sakurai, Y. *Polym J* 1991, 23, 1179-1189.

Katono, H., Maruyama, A., Sanui, K., Ogata, N., Okano, T., Sakurai, Y. *J Control Rel* 1991, 16, 215-227 273:464-472

Gutowska, Y. H., Bae, H., Jacobs, J., Feijen, Sung Wan Kim, *Macromolecules*, 1994, 27, 4167.

Park, T. G., Choi, H. K. *Macromol. Rapid Commun.* 1998, 19, 167-172.

Hirotsu, S., Hirokawa, Y., Tanaka, T. *J. Chem. Phys.* 1987, 87, 1392.

Wu, C., Zhou, S. *Macromolecules* 1996, 29, 1574.

Benee, L. S., Snowden, M. J., Chowdhry, B. Z., *Langmuir*, 2002, 18, 6025.

Routh, A. F., Vincent, B., *Langmuir*, 2002, 18, 5366-5369.

Woodward, N. C., Chowdhry, B. Z., Snowden, M. J., Leharne, S. A., Griffiths, P. C., Winnington, A. L., *Langmuir*, 2003, 19, 3202-3211.

Gao, J., Frisken, B. J., *Langmuir*, 2003, 19, 5217-5222.

Bouillot, P., Vincent, B. *Colloid and Polymer Science* 2000, 278, 74-79.

Jones, C. D., Lyon, L. A. *Macromolecules* 2000, 33, 8301-8306

T. Kato, M. Yokoyama, A. Takahashi, *Colloid & Polym. Sci.* 1978, 256, 15.

M. Almgren, P. Bahadur, M. Jansson, P. Li, W. Brown, A. J. Bahadur, *Colloid & Interface Sci.* 1992, 151, 157.

P. Alexandridis, T. A. Hatton, *Colloidal Surfaces A: Physicochem. Eng. Aspects* 1995, 96, 1-46.

C. K. Han, Y. H. Bae, *Polymer* 1998, 39, 2809-2814.

B. Jeong, S. W. Kim, Y. H. Bae, *Adv. Drug Del. Rev.* 2002, 54, 37-51.

R. Yoshida, K. Uchida, Y. Kaneko, K. Sakai, A. Kikuchi, Y. Sakurai, and T. Okano, Comb-type grafted hydrogels with rapid de-swelling response to temperature changes, Nature 374 (1995) 240.

Y. H. Bae, T. Okano, and S. W. Kim, Thermo-sensitive polymers as on-off switches for drug release, Makromolecular Chemistry Rapid Communication 8 (1987) 481

T. Okano, Y. H. Bae, H. Jacobs, and S. W. Kim, Thermally on-off switching polymers for drug permeation and release, Journal of Controlled Release 11 (1990) 255

Y. H. Bae, T. Okano, and S. W. Kim, "On-off" thermocontrol of solute transport. I. Temperature dependence of swelling of N-isopropylacrylamide networks modified with hydrophobic components in water, Pharmaceutical Research 8 (1991) 531

Y. H. Bae, T. Okano, and S. W. Kim, "On-off" thermocontrol of solute transport. II. Solute release from thermosensitive hydrogels, Pharmaceutical Research 8 (1991) 624.

Y. H. Bae, T. Okano, S. W. Kim, Hydrogels, Swelling and Drug Loading and Release, Pharma. Res. 9 (1992) 283.

L. E. Bromberg, E. S. Ron, Temperature-responsive gels and thermogelling polymer matrices for protein and peptide delivery, Adv. Drug Deliv. Rev. 31 (1998) 197.

R. H., Pelton, P. Chibante, *Colloids and Surfaces* 1986, 20, 247-256

Pelton, R. *Adv. Colloid Interface Sci.* 2000, 85, 1-33

Chu, B. *Laser Light Scattering*, $2^{nd}$ ed., (Academic Press: New York), 1990.

J. Z. Wu, B. Zhou, Z. B. Hu, *Phys. Rev. Lett.* 2003, 90, 048304.

J. Z. Wu, G. Huang, Z. B. Hu, *Macromolecules* 2003, 36, 440-448.

Gao, J., Hu, Z., *Langmuir*, 2002, 18 (4), 1360-1367.

J. M. Weissman, H. B. Sunkara, A. S. Tse, S. A. Asher, *Science* 1996, 274, 959-960.

J. H. Holtz, S. A. Asher, *Nature* 1997, 389, 829-832. c) L. Liu, P. Li, and S. A. Asher, *Nature*, 397, 141-144 (1998).

K. Lee and S. A. Asher, *J. Am. Chem. Soc.*, 122, 9534-9537 (2000).

M. Hayakawa, T. Onda, T. Tanaka and K. Tsujii, Langmuir 1997, 13, 3595.

K. Tsujii, M. Hayakawa, T. Onda and T. Tanaka, Macromolecules 1997, 30, 7397.

J. Z. Wu, B. Zhou, Z. B. Hu, *Phys. Rev. Lett.* 2003, 90, 048304.

J. Z. Wu, G. Huang, Z. B. Hu, *Macromolecules* 2003, 36, 440-448

Z. B. Hu, X. H. Xia, Hydrogel nanoparticle dispersions with inverse thermoreversible gelation, Adv. Mat. 16 (2004) 305.

X. H. Xia, Z. B. Hu, Synthesis and light scattering study of nanoparticles with interpenetrating polymer networks, Langmuir 20 (2004) 2094.

F. Ilmain, T. Tanaka, E. Kokufuta, Volume transition in a gel driven by hydrogen bonding, Nature (London, United Kingdom) 349 (1991) 400.

A. Durand, D. Hourdet, Synthesis and thermoassociative properties in aqueous solution of graft copolymers containing poly(N-isopropylacrylamide) side chains, Polymer 40 (1999) 4941.

A. V. Kabanov, E. V. Batrakova, N. S. Melik-Nubarov, N. A. Fedoseev, T. Y. Dorodnich, A new class of drug carriers-Micelles of poly(oxyethylene)-poly(oxypropylene) block copolymers as microcontainers for drug targeting from blood and brain, J Control Rel 22 (1992) 141.

A. P. Sassi, A. J. Shaw, S. M. Han, H. W. Blanch and J. M. Prausnitz, Partitioning of proteins and small biomolecules in temperature- and pH-sensitive hydrogels, Polymer 37 (1996) 2151.

M. Palasis and S. H. Gehrke, Permeability of responsive poly (N-isopropylacrylamide) gel to solutes, Journal of Controlled Release 18 (1992) 1.

What is claimed is:

1. An aqueous dispersion of hydrogel interpenetrating polymer network of mono-dispersed nanoparticles, comprising:
    interpenetrating polymer network nanoparticles, wherein each IPN nanoparticle comprises a first polymer network interpenetrating a second polymer network; and
    an aqueous medium;
    wherein, the first polymer comprises poly(N-isopropylacrylamide) or hydroxypropylcellulose, and the second polymer comprises poly(acrylic acid);
    wherein, the IPN mono-dispersed nanoparticles are substantially free of a core-shell polymer configuration;
    and the aqueous dispersion of hydrogel nanoparticles can undergo a reversible gelation in response to a change in stimulus applied thereon; and
    wherein, the aqueous dispersion exhibits a change in particle size of less than 30 nm when the aqueous dispersion is heated from below a volume phase transition temperature to above a volume phase transition temperature at a concentration of $2.88 \times 10^{-5}$ g/ml.

2. The aqueous dispersion of hydrogel nanoparticles of claim 1, further comprising a biologically active material.

3. The aqueous dispersion of hydrogel nanoparticles of claim 2 wherein the biologically active material is: a drug, a pro-drug, a protein, a nucleic acid, or a mixture thereof.

4. The aqueous dispersion of hydrogel nanoparticles of claim 1, wherein the stimulus comprises a change in temperature.

5. The aqueous dispersion of hydrogel nanoparticles of claim 4, wherein the temperature change above a gelation temperature (Tg) induces a volume phase transition of the IPN nanoparticles, resulting in an inverse thermo-thickening property of the aqueous dispersion of hydrogel nanoparticles, and wherein above the Tg the first polymer network consists of crosslinked polymer chains inside each nanoparticle, and the second polymer network consists of a crosslinked system of the nanoparticles.

6. The aqueous dispersion of hydrogel nanoparticles of claim 5, wherein the inverse thermo-thickening property is a transformation from a low-viscous fluid to a gel when heated above the Tg.

7. The aqueous dispersion of hydrogel nanoparticles of claim 5, wherein the Tg is about 34° C.

8. The aqueous dispersion of hydrogel nanoparticles of claim 1, wherein the IPN nanoparticles have a uniformed sized hydrodynamic radius.

9. The aqueous dispersion of hydrogel nanoparticles of claim 1, wherein the IPN nanoparticles have an average hydrodynamic radius in the range from about 75 nm to about 200 nm.

10. The aqueous dispersion of hydrogel nanoparticles of claim 1, wherein the first polymer and second polymer in the IPN nanoparticles have weight ratio of about 1:1.88.

11. The aqueous dispersion of hydrogel nanoparticles of claim 1, wherein the first polymer network and the second polymer network have a total polymer concentration in the range of from about 1.25 wt % to about 5.25 wt %.

12. A method of preparing an interpenetrating polymer network (IPN) of mono-disperse nanoparticles, comprising:
    (a) providing a first mono-dispersed polymer prepared by mixing a first monomer, a surfactant, a first cross linking agent, and a first initiator at a first temperature wherein the first mono-dispersed polymer has a low critical solution temperature of between 28° C. and 45° C., the first polymerization temperature is above the LCST of the first mono-dispersed polymer;
    (b) adding to the first mono-dispersed polymer a second monomer, a second cross linking agent, a second initiator and an activator to form a nanoparticle solution, wherein the nanoparticle solution is an aqueous solution;
    (c) mixing the nanoparticle solution for a period of time at a second temperature to form the IPN of mono-disperse nanoparticles; and
    (d) isolating the IPN of mono-dispersed nanoparticles;
    wherein the first monomer, the first cross linking agent, the second monomer, and the second cross linking agent are substantially free from dissolved oxygen gas and wherein the first mono-dispersed polymer forms a first polymer network which interpenetrates a second polymer network formed by the second polymer wherein the IPN nanoparticles are substantially free of a core-shell configuration; and
    wherein the second temperature is below the low critical solution temperature of the first monodispersed polymer.

13. The method of claim 12, further comprising (e) mixing the isolated IPN of mono-dispersed nanoparticles with a biologically active material at a third temperature.

14. The method of claim 13, wherein the biologically active material is a drug, a pro-drug, a protein, or a nucleic acid.

15. The method of claim 13, wherein the third temperature is below a gelation temperature (Tg) of the IPN of mono-disperse nanoparticles in an aqueous mixture, and wherein above the Tg the first polymer network consists of crosslinked polymer chains inside each nanoparticle, and the second polymer network consists of a crosslinked system of the nanoparticles.

16. The method of claim 15 wherein the Tg is about 33° C.

17. The method of claim 12, wherein the first mono-disperse polymer comprises poly(N-isopropylacrylamide) or hydroxypropylcellulose.

18. The method of claim 12, wherein the second monomer comprises poly(acrylic acid).

19. The method of claim 12, wherein the first mono-dispersed polymer nanoparticle comprises poly(N-isopropylacrylamide) and the second monomer comprises poly(acrylic acid).

20. The method of claim 12, wherein the first cross linking agent comprises N,N'-methylenebisacrylamide; the second cross linking agent comprises N,N'-methylenebisacrylamide; the first initiator comprises potassium persulfate; the second initiator comprises ammonium persulfate; the surfactant comprises sodium dodecyl sulfate (SDS) and the activator comprises TEMED.

21. The method of claim 12, wherein the IPN of mono-dispersed nanoparticles have an average hydrodynamic radius in the range from about 75 nm to about 200 nm.

22. The method of claim 12, wherein the period of time is less than 130 minutes.

23. The method of claim 22, wherein the period of time is about 120 minutes.

24. The method of claim 12, wherein the first temperature is about 70° C.

25. The method of claim 12, wherein the second temperature is about 21° C.

26. A method of preparing a nanocluster of cross-linked interpenetrating polymer networks (IPN) of mono-dispersed nanoparticles, comprising:
  (a) providing an aqueous dispersion of IPN nanoparticles;
  (b) adding a first cross linking agent and a second cross linking agent to the dispersion of IPN nanoparticles, forming an IPN cross linking solution; and
  (c) heating the IPN cross linking solution to a first temperature for a period of time to form the nanocluster of cross-linked IPN nanoparticles;
  wherein, the IPN nanoparticles have a uniformed size and comprise a first polymer network interpenetrating a second polymer network and is substantially free from a shell and core-shell polymer configuration; the IPN nanoparticles can undergo a reversible gelation in response to a change in stimulus applied thereon; and
  wherein the IPN nanoparticles exhibit a change in particle size of less than 30 nm when the IPN nanoparticles are heated from below a volume phase transition temperature to above a volume phase transition temperature at a concentration of $2.88 \times 10^{-5}$ g/ml.

27. The method of claim 26, further comprising (d) mixing the nanocluster of cross-linked IPN's with a biologically active material at a second temperature.

28. The method of claim 27, wherein the biologically active material is a drug, a pro-drug, a protein, a nucleic acid, or a mixture thereof.

29. The method of claim 27, wherein the second temperature is below a gelation temperature (Tg) of the nanocluster of cross-linked IPN nanoparticles in an aqueous dispersion.

30. The method of claim 29, wherein the Tg is about 33° C.

31. The method of claim 26, wherein the first polymer comprises poly-isopropylacrylamide) and the second polymer comprises poly(acrylic acid).

32. The method of claim 26, wherein the first cross linking agent comprises 1-ethyl-3(3-dimethylaminopropyl) carbodiimide hydrochloride (EDAC); and the second cross linking agent comprises adipic acid dihydrazide.

33. The method of claim 26, wherein the nanocluster of cross-linked IPN's an average hydrodynamic radius in the range from about 155 nm to about 250 nm.

34. The method of claim 33, wherein the nanocluster of cross-linked IPN's have an average hydrodynamic radius in the range from about 225 nm to about 240 nm.

35. The method of claim 26, wherein the period of time is about 25 to about 45 minutes.

36. The method of claim 35, wherein the period of time is about 33 to about 37 minutes.

37. The method of claim 26, wherein the first temperature is about 44° C.

38. A nanocluster of cross-linked interpenetrating polymer network (IPN) of mono-dispersed nanoparticles, comprising: at least two IPN nanoparticles linked by a cross-linking group; wherein, the each IPN nanoparticle have a uniformed size and comprise a first polymer network interpenetrating a second polymer network and is substantially free from a core-shell polymer configuration.

39. The nanocluster of claim 38, further comprising a biologically active material.

40. The nanocluster of claim 39, wherein the biologically active material is a drug, a pro-drug, a protein, a nucleic acid, or a mixture thereof.

41. The nanocluster of claim 38, wherein the first polymer comprises poly(N-isopropylacrylamide) and the second polymer comprises poly(acrylic acid).

42. The nanocluster of claim 38, wherein the cross linking group comprises adipic acid dihydrazide.

43. The nanocluster of claim 38, wherein the uniformed sized nanoparticles have an average hydrodynamic radius in the range from about 155 nm to about 1000 nm.

44. The nanocluster of claim 43, wherein the nanoparticles have an average hydrodynamic radius in the range from about 180 nm to about 250 nm.

* * * * *